(12) United States Patent
Konishi et al.

(10) Patent No.: US 8,703,466 B2
(45) Date of Patent: Apr. 22, 2014

(54) 2-DEOXY-SCYLLO-INOSOSE SYNTHASE

(75) Inventors: Kazunobu Konishi, Tokyo (JP);
Shinichi Imazu, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/258,932

(22) PCT Filed: Mar. 26, 2010

(86) PCT No.: PCT/JP2010/002210
§ 371 (c)(1),
(2), (4) Date: Dec. 8, 2011

(87) PCT Pub. No.: WO2010/109916
PCT Pub. Date: Sep. 30, 2010

(65) Prior Publication Data
US 2012/0100584 A1    Apr. 26, 2012

(30) Foreign Application Priority Data

Mar. 26, 2009  (JP) ................. 2009-075802
Mar. 26, 2009  (JP) ................. 2009-075803
Mar. 26, 2009  (JP) ................. 2009-075804
Mar. 26, 2009  (JP) ................. 2009-075805
Mar. 26, 2009  (JP) ................. 2009-075806
Mar. 27, 2009  (JP) ................. 2009-078713

(51) Int. Cl.
   *C12P 7/26*    (2006.01)
(52) U.S. Cl.
   USPC ........................................ 435/232; 435/128
(58) Field of Classification Search
   USPC ................................. 435/128, 232
   See application file for complete search history.

(56) References Cited

U.S. PATENT DOCUMENTS

2010/0015672 A1    1/2010   Takagi et al.

FOREIGN PATENT DOCUMENTS

| CN | 101151368 A   | 3/2008  |
| JP | 2000-236881 A | 9/2000  |
| JP | 2006-262846 A | 10/2006 |
| WO | 2006-109479 A1 | 10/2006 |
| WO | 2006-112000 A1 | 10/2006 |

OTHER PUBLICATIONS

Sen et al., Appl. Biochem. Biotechnol., Developments in Directed Evolution for Improving Enzyme Functions. 2007, vol. 143: 212-223.*
Chica et al., Curr. Opin. Biotechnol., Semi-rational approaches to engineering enzyme activity: combining the benefits of directed evolution and rational design. 2005, vol. 16: 378-384.*
Vente et al., Sequence ID AED48355, B. circulans 2-deoxy-scyllo-inosose synthase. WO2005095591-A2 and embedded in the Office action.*
Flatt et al., Biosynthesis of aminocyclitol-aminoglycoside antibiotics and related compounds. Nat. Prod. Rep, 24: 358-392, 2007.*
Extended European Search Report issued in corresponding European Patent Application No. 10755718.3 dated Jan. 10, 2013.
Hirayama et al., "Role of glutamate 243 in the active site of 2-deoxy-scyllo-inosose synthase from *Bacillus circulans*," Bioorganic & Medicinal Chemistry 15: 418-423 (2007).
Nango et al., "Crystallization and X-ray analysis of 2-deoxy-scyllo-inosose synthase, the key enzyme in the biosynthesis of 2-deoxystreptamine-containing aminoglycoside antibiotics," Acta Crystallographica, 61: 709-711 (2005).
Hirayama et al. Biosythesis of 2-deoxystreptamine-containing antibiotics in *Streptoalloteichus hindustanus* JCM 3268: characterization of 2-deoxy-scyllo-inosose synthase, The Journal of Antibiotics 59, 358-361, 2006.
Kakinuma et al. An expeditious chemo-enzymatic route from glucose to catechol by the use of 2-deoxy-scyllo-inosose synthase, Tetrahedron Letters 41, 1935-1938, 2000.
Kogure et al. Efficient production of 2-deoxy-scyllo-inosose from d-glucose by metabolically engineered recombinant *Escherichia coli*, Journal of Biotechnology 129, 502-509, 2007.
Kudo et al. Molecular cloning of the gene for the key carbocycle-forming enzyme in the biosynthesis of 2-deoxystreptamine-containing aminocyclitol antibiotics and its comparison with dehydroquinate synthase, Journal of Antibiotics 52, 559-571, 1999.
Tamegai et al. Exploration of genes that encode a carbocycle-forming enzyme involved in biosynthesis of aminoglycoside antibiotics from the environmental DNA, Biosci. Biotechnol. Biochem., 70, 1711-1716, 2006.
Extended European Search Report issued in corresponding European Patent Application No. 10755718.3 dated Oct. 17, 2013.

* cited by examiner

*Primary Examiner* — Tekchand Saidha
*Assistant Examiner* — Rama P Ramanujam
(74) *Attorney, Agent, or Firm* — Morgan, Lewis & Bockius LLP

(57) ABSTRACT

An object of the present invention is to provide a DOI synthase having properties such as stability to heat and pH, which are superior to those of conventional enzymes, and a method for producing DOI using the above-mentioned enzyme. The present invention provides a 2-deoxy-scyllo-inosose synthase having the properties described in the following (1), (2), (4), (6) and (7), and also having the properties described in the following (3) and/or (5):

(1) action: the enzyme has a function to convert glucose-6-phosphate to 2-deoxy-scyllo-inosose;
(2) optimum pH range: pH 7.0 to 7.7;
(3) stable pH range: pH 6.0 to 8.0;
(4) optimum temperature range: 55° C. to 70° C.;
(5) stable temperature range: 20° C. to 46° C.;
(6) coenzyme used: $NAD^+$; and
(7) molecular weight: 39,000 to 42,000.

15 Claims, 7 Drawing Sheets

Figure 1. Optimum pH range of purified DOI synthase (DOIS-1) (Example 3)
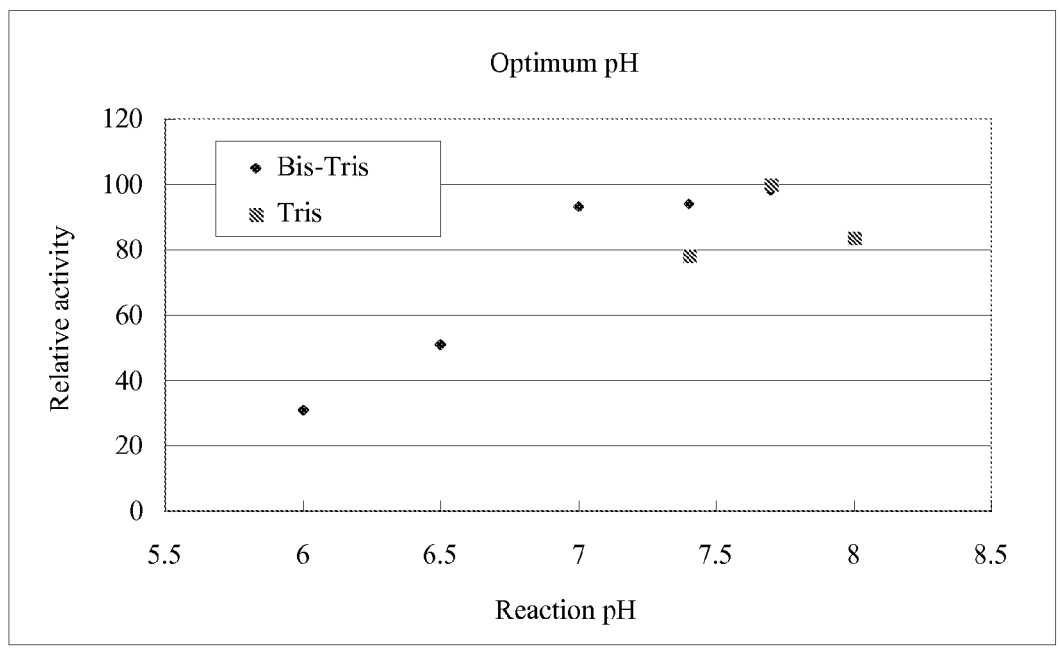

Figure 2. Stable pH range of purified DOI synthase (DOIS-1) (Example 3)
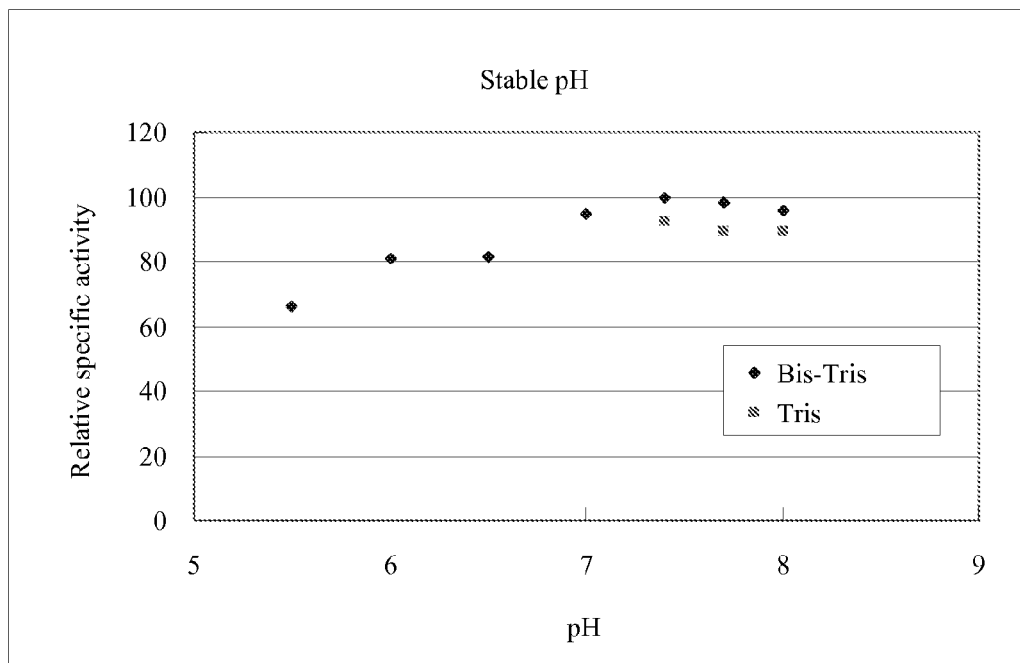

Figure 3. Optimum temperature range of purified DOI synthase (DOIS-1) (Example 3)
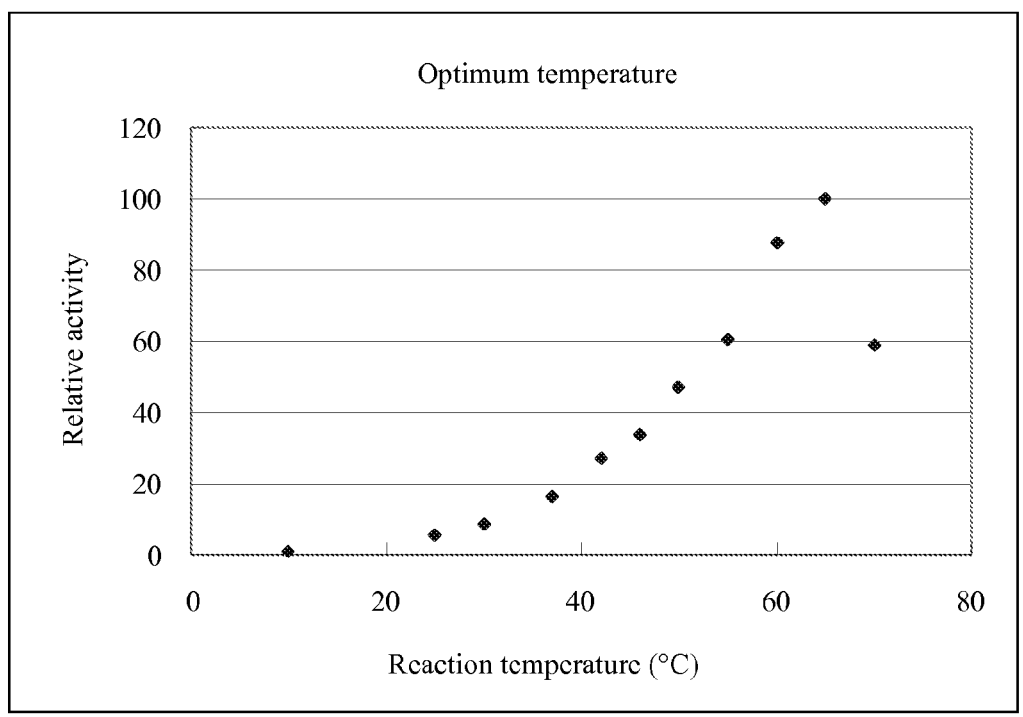

Figure 4. Stable temperature range of purified DOI synthase (DOIS-1) (Example 3)
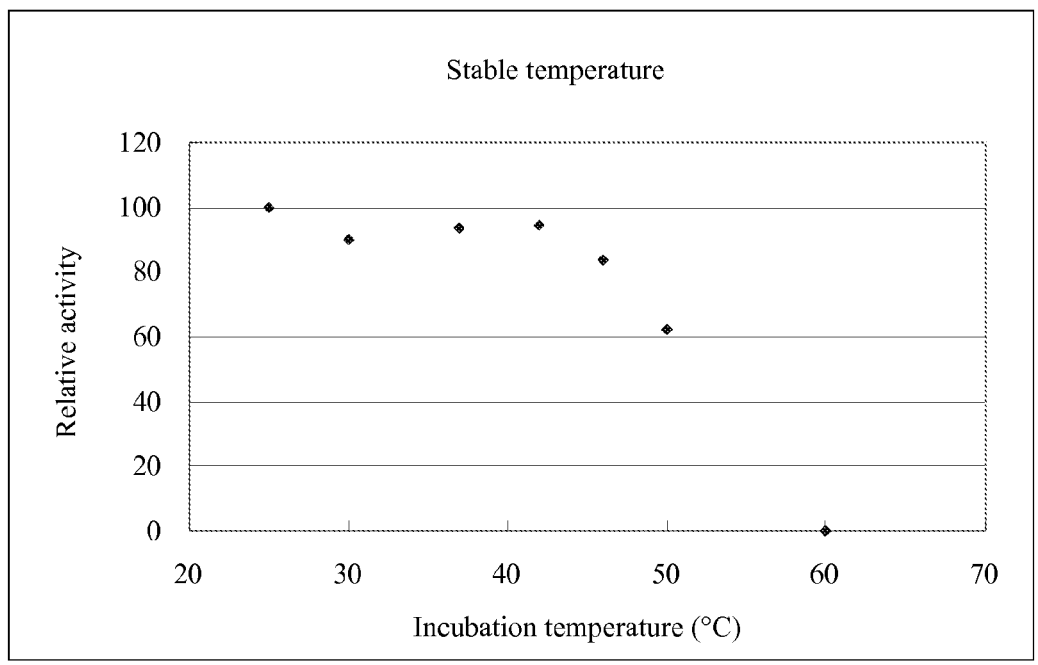

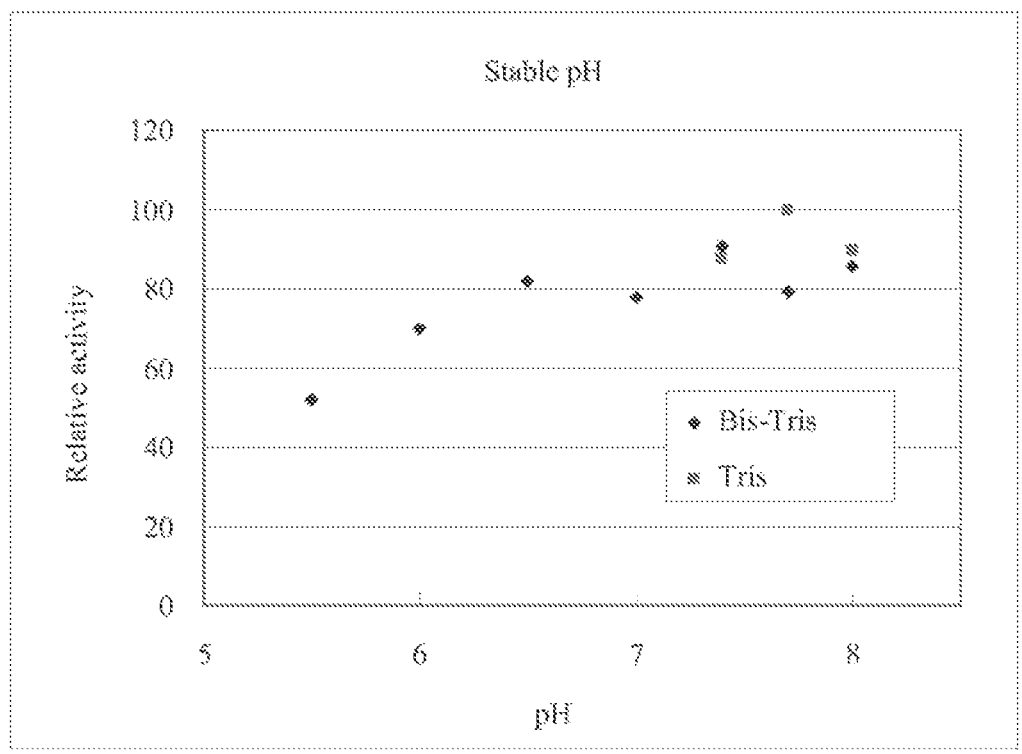
Figure 5. Stable pH range of purified DOI synthase (DOIS-5) (Example 5)

Figure 6. Stable temperature range of purified DOI synthase (BtrC)
(Comparative Example 1)
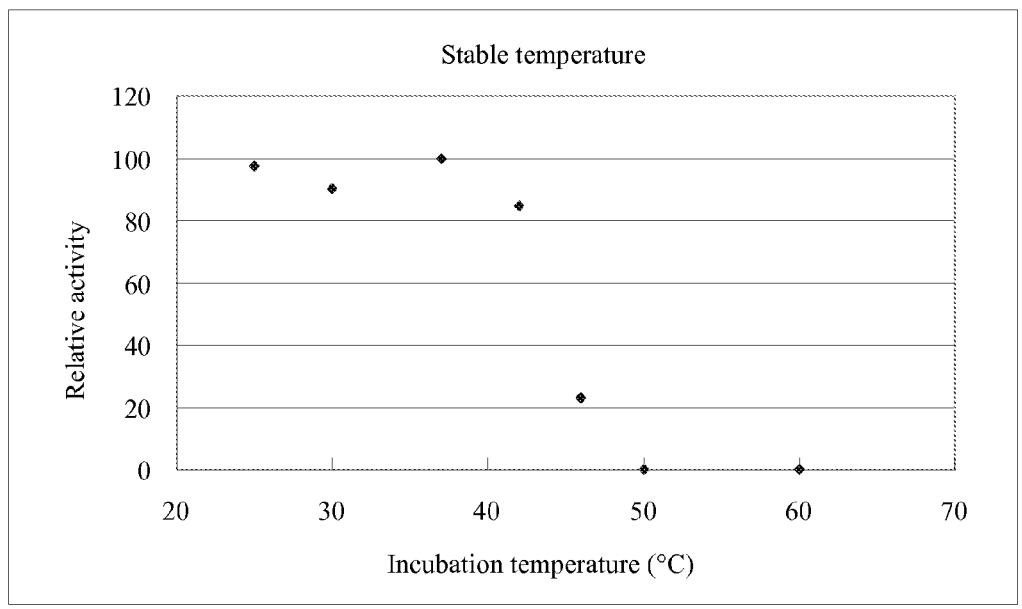

Figure 7. Stable pH range of purified DOI synthase (BtrC)
(Comparative Example 1)
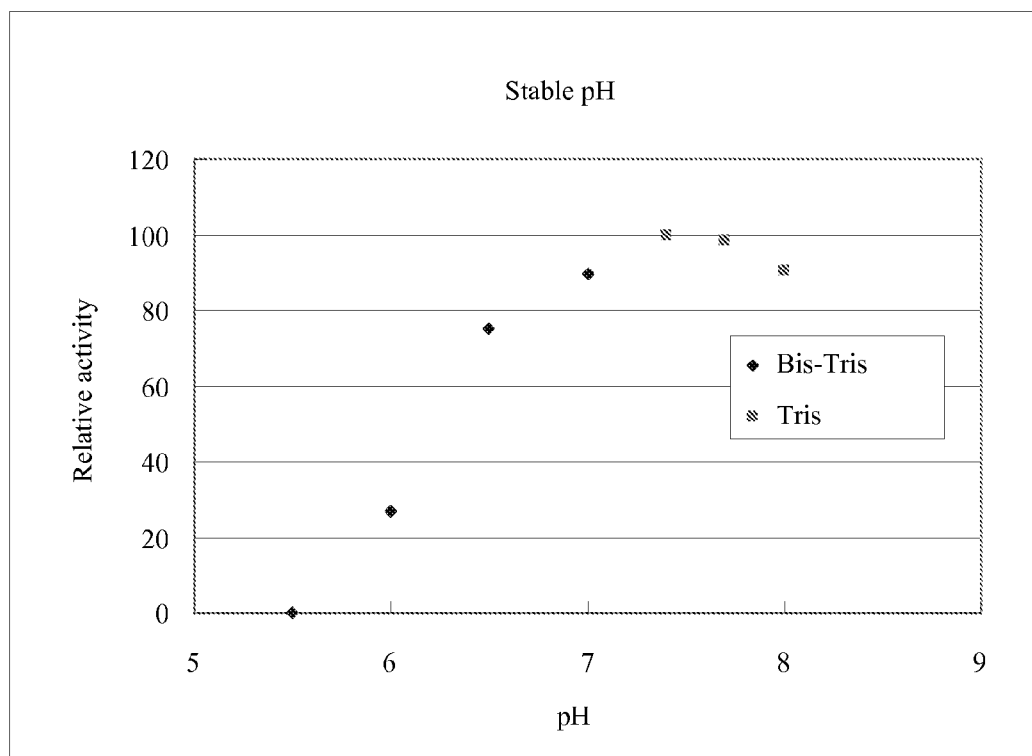

SEQUENCE LISTING

```
<160> NUMBER OF SEQ ID NOS: 16

<210> SEQ ID NO 1
<211> LENGTH: 1107
<212> TYPE: DNA
<213> ORGANISM: Paenibacillus sp.
<220> FEATURE:
```

<221> NAME/KEY: CDS
<222> LOCATION: (1)..(1107)

<400> SEQUENCE: 1

```
atg acg act aaa caa att tgt ttt gcg gac cgg tgt ttt aac ttt gca      48
Met Thr Thr Lys Gln Ile Cys Phe Ala Asp Arg Cys Phe Asn Phe Ala
1               5                   10                  15 ttc ggc gaa cag att ttg gaa tcg att gcc gcc tat att cac cgg gat      96
Phe Gly Glu Gln Ile Leu Glu Ser Ile Ala Ala Tyr Ile His Arg Asp
            20                  25                  30 gaa ttc gat caa tat atc gtg att tcg gac tcg ggg gta ccg gac tcg     144
Glu Phe Asp Gln Tyr Ile Val Ile Ser Asp Ser Gly Val Pro Asp Ser
        35                  40                  45 att gtt cat cat gcg gcc gaa tac ttc ggc aga ctc gcc cct gta cat     192
Ile Val His His Ala Ala Glu Tyr Phe Gly Arg Leu Ala Pro Val His
    50                  55                  60 att ctt cgc ttt cag ggc gga gaa gaa tac aaa aca ctt gca acc gtg     240
Ile Leu Arg Phe Gln Gly Gly Glu Glu Tyr Lys Thr Leu Ala Thr Val
65                  70                  75                  80 aca aat ttg caa gag cag gca att gct ctg gga gcc aac cga aga acc     288
Thr Asn Leu Gln Glu Gln Ala Ile Ala Leu Gly Ala Asn Arg Arg Thr
                85                  90                  95 gct atc gta gcg gtt ggc gga ggg tta acc gga aac gtt gcc gga gtg     336
Ala Ile Val Ala Val Gly Gly Gly Leu Thr Gly Asn Val Ala Gly Val
            100                 105                 110 gcg gcc ggc atg atg ttt cgc ggg att gcg ctt att cac gtt ccg acc     384
Ala Ala Gly Met Met Phe Arg Gly Ile Ala Leu Ile His Val Pro Thr
        115                 120                 125 acg ttt ttg gcg gcc tcc gat tcg gtt ctt tcg att aag cag gct gtt     432
Thr Phe Leu Ala Ala Ser Asp Ser Val Leu Ser Ile Lys Gln Ala Val
    130                 135                 140 aat tta acg agc gga aag aac ctg gtc ggc ttt tat tat ccg cca cgc     480
Asn Leu Thr Ser Gly Lys Asn Leu Val Gly Phe Tyr Tyr Pro Pro Arg
145                 150                 155                 160 ttc gtg ttc gcc gat acc cga atc ttg gcg gag tcg ccg ccc cgt cag     528
Phe Val Phe Ala Asp Thr Arg Ile Leu Ala Glu Ser Pro Pro Arg Gln
                165                 170                 175 gtg aaa gcg gga atg tgc gag ctg gta aaa aat atg ctg att ctg gaa     576
Val Lys Ala Gly Met Cys Glu Leu Val Lys Asn Met Leu Ile Leu Glu
            180                 185                 190 aac gag cac atg gaa ttt aca gag gat gat tta aat gca gcc aat gtg     624
Asn Glu His Met Glu Phe Thr Glu Asp Asp Leu Asn Ala Ala Asn Val
        195                 200                 205 tat act ccg agg cag ctg gag acg ttt atc aac ttc tgc ata tcg gcc     672
Tyr Thr Pro Arg Gln Leu Glu Thr Phe Ile Asn Phe Cys Ile Ser Ala
    210                 215                 220 aaa atg tcg gta tta agc gaa gat att tac gag aaa aag aag ggc ctg     720
Lys Met Ser Val Leu Ser Glu Asp Ile Tyr Glu Lys Lys Lys Gly Leu
225                 230                 235                 240 atc ttt gag tac ggc cat acg atc ggt cat gcg atc gag ctt gcc gag     768
Ile Phe Glu Tyr Gly His Thr Ile Gly His Ala Ile Glu Leu Ala Glu
                245                 250                 255 cag gga ggg atc acg cac gga gaa gcc att gca gtg ggc atg att tac     816
Gln Gly Gly Ile Thr His Gly Glu Ala Ile Ala Val Gly Met Ile Tyr
            260                 265                 270 gcc gct aaa ata gcg aac cgg atg aac ctg ctc tcc gaa cag gac gtg     864
Ala Ala Lys Ile Ala Asn Arg Met Asn Leu Leu Ser Glu Gln Asp Val
        275                 280                 285 tcc acc cat tac tgg ctt tta aat aaa atc ggg gcc ttg cag gag ctt     912
Ser Thr His Tyr Trp Leu Leu Asn Lys Ile Gly Ala Leu Gln Glu Leu
    290                 295                 300
```

```
ccg ctc cga gcg gac gcg gat tcg gtc ttc cat tat tta atc cac gat      960
Pro Leu Arg Ala Asp Ala Asp Ser Val Phe His Tyr Leu Ile His Asp
305                 310                 315                 320 aac aag agg ggc tac att aag ctg gat gag gat aat ttg ggt atg att     1008
Asn Lys Arg Gly Tyr Ile Lys Leu Asp Glu Asp Asn Leu Gly Met Ile
                325                 330                 335 tta ctt gag gga atc ggt cga ccg gcg gtt cat aac caa tcg ctg ctt     1056
Leu Leu Glu Gly Ile Gly Arg Pro Ala Val His Asn Gln Ser Leu Leu
            340                 345                 350 aca ccg gtc aag aaa tcg ctc ata aaa gaa gtg atc cgg gaa ggg ctg     1104
Thr Pro Val Lys Lys Ser Leu Ile Lys Glu Val Ile Arg Glu Gly Leu
        355                 360                 365 taa                                                                  1107
```

<210> SEQ ID NO 2
<211> LENGTH: 368
<212> TYPE: PRT
<213> ORGANISM: Paenibacillus sp.

<400> SEQUENCE: 2

```
Met Thr Thr Lys Gln Ile Cys Phe Ala Asp Arg Cys Phe Asn Phe Ala
1               5                   10                  15

Phe Gly Glu Gln Ile Leu Glu Ser Ile Ala Ala Tyr Ile His Arg Asp
            20                  25                  30

Glu Phe Asp Gln Tyr Ile Val Ile Ser Asp Ser Gly Val Pro Asp Ser
        35                  40                  45

Ile Val His His Ala Ala Glu Tyr Phe Gly Arg Leu Ala Pro Val His
    50                  55                  60

Ile Leu Arg Phe Gln Gly Gly Glu Glu Tyr Lys Thr Leu Ala Thr Val
65                  70                  75                  80

Thr Asn Leu Gln Glu Gln Ala Ile Ala Leu Gly Ala Asn Arg Arg Thr
                85                  90                  95

Ala Ile Val Ala Val Gly Gly Gly Leu Thr Gly Asn Val Ala Gly Val
            100                 105                 110

Ala Ala Gly Met Met Phe Arg Gly Ile Ala Leu Ile His Val Pro Thr
        115                 120                 125

Thr Phe Leu Ala Ala Ser Asp Ser Val Leu Ser Ile Lys Gln Ala Val
    130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ala Glu Ser Pro Pro Arg Gln
                165                 170                 175

Val Lys Ala Gly Met Cys Glu Leu Val Lys Asn Met Leu Ile Leu Glu
            180                 185                 190

Asn Glu His Met Glu Phe Thr Glu Asp Asp Leu Asn Ala Ala Asn Val
        195                 200                 205

Tyr Thr Pro Arg Gln Leu Glu Thr Phe Ile Asn Phe Cys Ile Ser Ala
    210                 215                 220

Lys Met Ser Val Leu Ser Glu Asp Ile Tyr Glu Lys Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
            260                 265                 270

Ala Ala Lys Ile Ala Asn Arg Met Asn Leu Leu Ser Glu Gln Asp Val
        275                 280                 285
```

```
Ser Thr His Tyr Trp Leu Leu Asn Lys Ile Gly Ala Leu Gln Glu Leu
    290                 295                 300

Pro Leu Arg Ala Asp Ala Asp Ser Val Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Glu Gly Ile Gly Arg Pro Ala Val His Asn Gln Ser Leu Leu
            340                 345                 350

Thr Pro Val Lys Lys Ser Leu Ile Lys Glu Val Ile Arg Glu Gly Leu
        355                 360                 365

<210> SEQ ID NO 3
<211> LENGTH: 1113
<212> TYPE: DNA
<213> ORGANISM: Paenibacillus sp.
<220> FEATURE:
<221> NAME/KEY: CDS
<222> LOCATION: (1)..(1113)

<400> SEQUENCE: 3
```

| | | | | | | | | | | | | | | | | |
|---|---|---|---|---|---|---|---|---|---|---|---|---|---|---|---|---|
| atg | acg | act | aaa | caa | att | tgt | ttt | gcg | gac | cgg | tgt | ttt | aac | ttt | gca | 48 |
| Met | Thr | Thr | Lys | Gln | Ile | Cys | Phe | Ala | Asp | Arg | Cys | Phe | Asn | Phe | Ala | |
| 1 | | | | 5 | | | | | 10 | | | | | 15 | | |
| ttc | ggc | gaa | cag | att | ttg | gaa | tcg | att | gcc | gcc | tat | att | cac | cgg | gat | 96 |
| Phe | Gly | Glu | Gln | Ile | Leu | Glu | Ser | Ile | Ala | Ala | Tyr | Ile | His | Arg | Asp | |
| | | | 20 | | | | | 25 | | | | | 30 | | | |
| gaa | ttc | gat | caa | tat | atc | gtg | att | tcg | gac | tcg | ggg | gta | ccg | gac | tcg | 144 |
| Glu | Phe | Asp | Gln | Tyr | Ile | Val | Ile | Ser | Asp | Ser | Gly | Val | Pro | Asp | Ser | |
| | 35 | | | | | 40 | | | | | 45 | | | | | |
| att | gtt | cat | cat | gcg | gcc | gaa | tac | ttc | ggc | aga | ctc | gcc | cct | gta | cat | 192 |
| Ile | Val | His | His | Ala | Ala | Glu | Tyr | Phe | Gly | Arg | Leu | Ala | Pro | Val | His | |
| 50 | | | | | 55 | | | | | 60 | | | | | | |
| att | ctt | cgc | ttt | cag | ggc | gga | gaa | gaa | tac | aaa | aca | ctt | gca | acc | gtg | 240 |
| Ile | Leu | Arg | Phe | Gln | Gly | Gly | Glu | Glu | Tyr | Lys | Thr | Leu | Ala | Thr | Val | |
| 65 | | | | | 70 | | | | | 75 | | | | | 80 | |
| aca | aat | ttg | caa | gag | cag | gca | att | gct | ctg | gga | gcc | aac | cga | aga | acc | 288 |
| Thr | Asn | Leu | Gln | Glu | Gln | Ala | Ile | Ala | Leu | Gly | Ala | Asn | Arg | Arg | Thr | |
| | | | | 85 | | | | | 90 | | | | | 95 | | |
| gct | atc | gta | gcg | gtt | ggc | gga | ggg | tta | acc | gga | aac | gtt | gcc | gga | gtg | 336 |
| Ala | Ile | Val | Ala | Val | Gly | Gly | Gly | Leu | Thr | Gly | Asn | Val | Ala | Gly | Val | |
| | | | 100 | | | | | 105 | | | | | 110 | | | |
| gcg | gcc | ggc | atg | atg | ttt | cgc | ggg | att | gcg | ctt | att | cac | gtt | ccg | acc | 384 |
| Ala | Ala | Gly | Met | Met | Phe | Arg | Gly | Ile | Ala | Leu | Ile | His | Val | Pro | Thr | |
| | 115 | | | | | 120 | | | | | 125 | | | | | |
| acg | ttt | ttg | gcg | gcc | tcc | gat | tcg | gtt | ctt | tcg | att | aag | cag | gct | gtt | 432 |
| Thr | Phe | Leu | Ala | Ala | Ser | Asp | Ser | Val | Leu | Ser | Ile | Lys | Gln | Ala | Val | |
| 130 | | | | | 135 | | | | | 140 | | | | | | |
| aat | tta | acg | agc | gga | aag | aac | ctg | gtc | ggc | ttt | tat | tat | ccg | cca | cgc | 480 |
| Asn | Leu | Thr | Ser | Gly | Lys | Asn | Leu | Val | Gly | Phe | Tyr | Tyr | Pro | Pro | Arg | |
| 145 | | | | | 150 | | | | | 155 | | | | | 160 | |
| ttc | gtg | ttc | gcc | gat | acc | cga | atc | ttg | gcg | gag | tcg | ccg | ccc | cgt | cag | 528 |
| Phe | Val | Phe | Ala | Asp | Thr | Arg | Ile | Leu | Ala | Glu | Ser | Pro | Pro | Arg | Gln | |
| | | | 165 | | | | | 170 | | | | | 175 | | | |
| gtg | aaa | gcg | gga | atg | tgc | gag | ctg | gta | aaa | aat | atg | ctg | att | ctg | gaa | 576 |
| Val | Lys | Ala | Gly | Met | Cys | Glu | Leu | Val | Lys | Asn | Met | Leu | Ile | Leu | Glu | |
| | | | 180 | | | | | 185 | | | | | 190 | | | |
| aac | gag | cac | atg | gaa | ttt | aca | gag | gat | gat | tta | aat | gca | gcc | aat | gtg | 624 |
| Asn | Glu | His | Met | Glu | Phe | Thr | Glu | Asp | Asp | Leu | Asn | Ala | Ala | Asn | Val | |
| | 195 | | | | | 200 | | | | | 205 | | | | | |
| tat | act | ccg | agg | cag | ctg | gag | acg | ttt | atc | aac | ttc | tgc | ata | tcg | gcc | 672 |

```
Tyr Thr Pro Arg Gln Leu Glu Thr Phe Ile Asn Phe Cys Ile Ser Ala
    210                 215                 220 aaa atg tcg gta tta agc gaa gat att tac gag aaa aag aag ggc ctg      720
Lys Met Ser Val Leu Ser Glu Asp Ile Tyr Glu Lys Lys Lys Gly Leu
225                 230                 235                 240 atc ttt gag tac ggc cat acg atc ggt cat gcg atc gag ctt gcc gag      768
Ile Phe Glu Tyr Gly His Thr Ile Gly His Ala Ile Glu Leu Ala Glu
                245                 250                 255 cag gga ggg atc acg cac gga gaa gcc att gca gtg ggc atg att tac      816
Gln Gly Gly Ile Thr His Gly Glu Ala Ile Ala Val Gly Met Ile Tyr
            260                 265                 270 gcc gct aaa ata gcg aac cgg atg aac ctg ctg tcc gaa cag gac gtg      864
Ala Ala Lys Ile Ala Asn Arg Met Asn Leu Leu Ser Glu Gln Asp Val
        275                 280                 285 tcc acc cat tac tgg ctt tta aat aaa atc ggg gcc ttg cag gag ctt      912
Ser Thr His Tyr Trp Leu Leu Asn Lys Ile Gly Ala Leu Gln Glu Leu
    290                 295                 300 ccg ctc cga gcg gac gcg gat tcg gtc ttc cat tat tta atc cac gat      960
Pro Leu Arg Ala Asp Ala Asp Ser Val Phe His Tyr Leu Ile His Asp
305                 310                 315                 320 aac aag agg ggc tac att aag ctg gat gag gat aat ttg ggt atg att     1008
Asn Lys Arg Gly Tyr Ile Lys Leu Asp Glu Asp Asn Leu Gly Met Ile
                325                 330                 335 tta ctt gag gga atc ggt cga ccg gcg gtt cat aac caa tcg ctg ctt     1056
Leu Leu Glu Gly Ile Gly Arg Pro Ala Val His Asn Gln Ser Leu Leu
            340                 345                 350 aca ccg gtc aag aaa tcg ctc ata aaa gaa gtg atc cgg gaa ggg ctg     1104
Thr Pro Val Lys Lys Ser Leu Ile Lys Glu Val Ile Arg Glu Gly Leu
        355                 360                 365 tgg gga tga                                                         1113
Trp Gly
    370

<210> SEQ ID NO 4
<211> LENGTH: 370
<212> TYPE: PRT
<213> ORGANISM: Paenibacillus sp.

<400> SEQUENCE: 4

Met Thr Thr Lys Gln Ile Cys Phe Ala Asp Arg Cys Phe Asn Phe Ala
1               5                   10                  15

Phe Gly Glu Gln Ile Leu Glu Ser Ile Ala Ala Tyr Ile His Arg Asp
                20                  25                  30

Glu Phe Asp Gln Tyr Ile Val Ile Ser Asp Ser Gly Val Pro Asp Ser
            35                  40                  45

Ile Val His His Ala Ala Glu Tyr Phe Gly Arg Leu Ala Pro Val His
50                  55                  60

Ile Leu Arg Phe Gln Gly Gly Glu Glu Tyr Lys Thr Leu Ala Thr Val
65                  70                  75                  80

Thr Asn Leu Gln Glu Gln Ala Ile Ala Leu Gly Ala Asn Arg Arg Thr
                85                  90                  95

Ala Ile Val Ala Val Gly Gly Gly Leu Thr Gly Asn Val Ala Gly Val
            100                 105                 110

Ala Ala Gly Met Met Phe Arg Gly Ile Ala Leu Ile His Val Pro Thr
        115                 120                 125

Thr Phe Leu Ala Ala Ser Asp Ser Val Leu Ser Ile Lys Gln Ala Val
    130                 135                 140

Asn Leu Thr Ser Gly Lys Asn Leu Val Gly Phe Tyr Tyr Pro Pro Arg
145                 150                 155                 160
```

-continued

```
Phe Val Phe Ala Asp Thr Arg Ile Leu Ala Glu Ser Pro Pro Arg Gln
                165                 170                 175
Val Lys Ala Gly Met Cys Glu Leu Val Lys Asn Met Leu Ile Leu Glu
            180                 185                 190
Asn Glu His Met Glu Phe Thr Glu Asp Leu Asn Ala Ala Asn Val
        195                 200                 205
Tyr Thr Pro Arg Gln Leu Glu Thr Phe Ile Asn Phe Cys Ile Ser Ala
    210                 215                 220
Lys Met Ser Val Leu Ser Glu Asp Ile Tyr Glu Lys Lys Gly Leu
225                 230                 235                 240
Ile Phe Glu Tyr Gly His Thr Ile Gly His Ala Ile Glu Leu Ala Glu
                245                 250                 255
Gln Gly Gly Ile Thr His Gly Glu Ala Ile Ala Val Gly Met Ile Tyr
            260                 265                 270
Ala Ala Lys Ile Ala Asn Arg Met Asn Leu Leu Ser Glu Gln Asp Val
        275                 280                 285
Ser Thr His Tyr Trp Leu Leu Asn Lys Ile Gly Ala Leu Gln Glu Leu
    290                 295                 300
Pro Leu Arg Ala Asp Ala Asp Ser Val Phe His Tyr Leu Ile His Asp
305                 310                 315                 320
Asn Lys Arg Gly Tyr Ile Lys Leu Asp Glu Asp Asn Leu Gly Met Ile
                325                 330                 335
Leu Leu Glu Gly Ile Gly Arg Pro Ala Val His Asn Gln Ser Leu Leu
            340                 345                 350
Thr Pro Val Lys Lys Ser Leu Ile Lys Glu Val Ile Arg Glu Gly Leu
        355                 360                 365
Trp Gly
    370

<210> SEQ ID NO 5
<211> LENGTH: 1107
<212> TYPE: DNA
<213> ORGANISM: Paenibacillus sp.
<220> FEATURE:
<221> NAME/KEY: CDS
<222> LOCATION: (1)..(1107)

<400> SEQUENCE: 5 atg acg act aaa caa att tgt ttt gcg gac cgg tgt ttt aac ttt gca     48
Met Thr Thr Lys Gln Ile Cys Phe Ala Asp Arg Cys Phe Asn Phe Ala
1               5                   10                  15 ttc ggc gaa cag att ttg gaa tcg att gcc gcc tat att cac cgg gat     96
Phe Gly Glu Gln Ile Leu Glu Ser Ile Ala Ala Tyr Ile His Arg Asp
            20                  25                  30 gaa ttc gat caa tat atc atg att tcg gac tcg ggg gta ccg gac tcg    144
Glu Phe Asp Gln Tyr Ile Met Ile Ser Asp Ser Gly Val Pro Asp Ser
        35                  40                  45 att gtt cat cat gcg gcc gaa tac ttc ggc aga ctc gcc cct gta cat    192
Ile Val His His Ala Ala Glu Tyr Phe Gly Arg Leu Ala Pro Val His
    50                  55                  60 att ctt cgc ttt cag ggc gga gaa gaa tac aaa aca ctt gca acc gtg    240
Ile Leu Arg Phe Gln Gly Gly Glu Glu Tyr Lys Thr Leu Ala Thr Val
65                  70                  75                  80 aca aat ttg caa gag cag gca att gct ctg gga gcc aac cga aga acc    288
Thr Asn Leu Gln Glu Gln Ala Ile Ala Leu Gly Ala Asn Arg Arg Thr
                85                  90                  95 gct atc gta gcg gtt ggc gga ggg tta acc gga aac gtt gcc gga gtg    336
Ala Ile Val Ala Val Gly Gly Gly Leu Thr Gly Asn Val Ala Gly Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | gcc | ggc | atg | atg | ttt | cgc | ggg | att | gcg | ctt | att | cac | gtt | ccg | acc | 384  |
| Ala | Ala | Gly | Met | Met | Phe | Arg | Gly | Ile | Ala | Leu | Ile | His | Val | Pro | Thr |      |
|     |     | 115 |     |     |     | 120 |     |     |     | 125 |     |     |     |     |     |      |
| acg | ttt | ttg | gcg | gcc | tcc | gat | tcg | gtt | ctt | tcg | att | aag | cag | gct | gtt | 432  |
| Thr | Phe | Leu | Ala | Ala | Ser | Asp | Ser | Val | Leu | Ser | Ile | Lys | Gln | Ala | Val |      |
|     | 130 |     |     |     |     | 135 |     |     |     |     | 140 |     |     |     |     |      |
| aat | tta | acg | agc | gga | aag | aac | ctg | gtc | ggc | ttt | tat | tat | ccg | cca | cgc | 480  |
| Asn | Leu | Thr | Ser | Gly | Lys | Asn | Leu | Val | Gly | Phe | Tyr | Tyr | Pro | Pro | Arg |      |
| 145 |     |     |     |     | 150 |     |     |     |     | 155 |     |     |     |     | 160 |      |
| ttc | gtg | ttc | gcc | gat | acc | cga | atc | ttg | gcg | gag | tcg | ccg | ccc | cgt | cag | 528  |
| Phe | Val | Phe | Ala | Asp | Thr | Arg | Ile | Leu | Ala | Glu | Ser | Pro | Pro | Arg | Gln |      |
|     |     |     |     | 165 |     |     |     |     | 170 |     |     |     |     | 175 |     |      |
| gtg | aaa | gcg | gga | atg | tgc | gag | ctg | gta | aaa | aat | atg | ctg | att | ctg | gaa | 576  |
| Val | Lys | Ala | Gly | Met | Cys | Glu | Leu | Val | Lys | Asn | Met | Leu | Ile | Leu | Glu |      |
|     |     |     | 180 |     |     |     |     | 185 |     |     |     |     | 190 |     |     |      |
| aac | gag | cac | atg | gaa | ttt | aca | gag | gat | gat | tta | aat | tca | gcc | aat | gtg | 624  |
| Asn | Glu | His | Met | Glu | Phe | Thr | Glu | Asp | Asp | Leu | Asn | Ser | Ala | Asn | Val |      |
|     |     |     | 195 |     |     |     | 200 |     |     |     |     | 205 |     |     |     |      |
| tat | tct | ccg | aag | cag | ctg | gag | acg | ttt | atc | aac | ttc | tgc | ata | tcg | gcc | 672  |
| Tyr | Ser | Pro | Lys | Gln | Leu | Glu | Thr | Phe | Ile | Asn | Phe | Cys | Ile | Ser | Ala |      |
|     | 210 |     |     |     |     | 215 |     |     |     |     | 220 |     |     |     |     |      |
| aaa | atg | tcg | gta | tta | agc | gaa | gat | att | tac | gag | aaa | aag | aag | ggc | ctg | 720  |
| Lys | Met | Ser | Val | Leu | Ser | Glu | Asp | Ile | Tyr | Glu | Lys | Lys | Lys | Gly | Leu |      |
| 225 |     |     |     |     | 230 |     |     |     |     | 235 |     |     |     |     | 240 |      |
| atc | ttt | gag | tac | ggc | cat | acg | atc | ggt | cat | gcg | atc | gag | ctt | gcc | gag | 768  |
| Ile | Phe | Glu | Tyr | Gly | His | Thr | Ile | Gly | His | Ala | Ile | Glu | Leu | Ala | Glu |      |
|     |     |     |     | 245 |     |     |     |     | 250 |     |     |     |     | 255 |     |      |
| cag | gga | ggg | atc | acg | cac | gga | gaa | gcc | att | gca | gtg | ggc | atg | att | tac | 816  |
| Gln | Gly | Gly | Ile | Thr | His | Gly | Glu | Ala | Ile | Ala | Val | Gly | Met | Ile | Tyr |      |
|     |     |     | 260 |     |     |     |     | 265 |     |     |     |     | 270 |     |     |      |
| gcc | gct | aaa | ata | gcg | aac | cgg | atg | aac | ctg | ctg | tcc | gaa | cag | gac | gtg | 864  |
| Ala | Ala | Lys | Ile | Ala | Asn | Arg | Met | Asn | Leu | Leu | Ser | Glu | Gln | Asp | Val |      |
|     |     | 275 |     |     |     |     | 280 |     |     |     |     | 285 |     |     |     |      |
| tcc | acc | cat | tac | tgg | ctt | tta | aat | aaa | atc | ggg | gcc | ttg | cag | gag | ctt | 912  |
| Ser | Thr | His | Tyr | Trp | Leu | Leu | Asn | Lys | Ile | Gly | Ala | Leu | Gln | Glu | Leu |      |
|     | 290 |     |     |     |     | 295 |     |     |     |     | 300 |     |     |     |     |      |
| ccg | ctc | cga | gcg | gac | gcg | gat | tcg | gtc | ttc | cat | tat | tta | atc | cac | gat | 960  |
| Pro | Leu | Arg | Ala | Asp | Ala | Asp | Ser | Val | Phe | His | Tyr | Leu | Ile | His | Asp |      |
| 305 |     |     |     |     | 310 |     |     |     |     | 315 |     |     |     |     | 320 |      |
| aac | aag | agg | ggc | tac | att | aag | ctg | gat | gag | gat | aat | ttg | ggt | atg | att | 1008 |
| Asn | Lys | Arg | Gly | Tyr | Ile | Lys | Leu | Asp | Glu | Asp | Asn | Leu | Gly | Met | Ile |      |
|     |     |     |     | 325 |     |     |     |     | 330 |     |     |     |     | 335 |     |      |
| tta | ctt | gag | gga | atc | ggt | cga | ccg | gcg | gtt | cat | aac | caa | tcg | ctg | ctt | 1056 |
| Leu | Leu | Glu | Gly | Ile | Gly | Arg | Pro | Ala | Val | His | Asn | Gln | Ser | Leu | Leu |      |
|     |     |     | 340 |     |     |     |     | 345 |     |     |     |     | 350 |     |     |      |
| aca | ccg | gtc | aag | aaa | tcg | ctc | ata | aaa | gaa | gtg | atc | cgg | gaa | ggg | ctg | 1104 |
| Thr | Pro | Val | Lys | Lys | Ser | Leu | Ile | Lys | Glu | Val | Ile | Arg | Glu | Gly | Leu |      |
|     |     |     | 355 |     |     |     |     | 360 |     |     |     |     | 365 |     |     |      |
| taa |     |     |     |     |     |     |     |     |     |     |     |     |     |     |     | 1107 |

<210> SEQ ID NO 6
<211> LENGTH: 368
<212> TYPE: PRT
<213> ORGANISM: Paenibacillus sp.

<400> SEQUENCE: 6

Met Thr Thr Lys Gln Ile Cys Phe Ala Asp Arg Cys Phe Asn Phe Ala
1               5                   10                  15

Phe Gly Glu Gln Ile Leu Glu Ser Ile Ala Ala Tyr Ile His Arg Asp

|    |    |    | 20 |    |    |    | 25 |    |    |    | 30 |    |    |    |
|----|----|----|----|----|----|----|----|----|----|----|----|----|----|----|

Glu Phe Asp Gln Tyr Ile Met Ile Ser Asp Ser Gly Val Pro Asp Ser
            35                  40                  45

Ile Val His His Ala Ala Glu Tyr Phe Gly Arg Leu Ala Pro Val His
 50                  55                  60

Ile Leu Arg Phe Gln Gly Gly Glu Glu Tyr Lys Thr Leu Ala Thr Val
 65                  70                  75                  80

Thr Asn Leu Gln Glu Gln Ala Ile Ala Leu Gly Ala Asn Arg Arg Thr
                 85                  90                  95

Ala Ile Val Ala Val Gly Gly Leu Thr Gly Asn Val Ala Gly Val
                100                 105                 110

Ala Ala Gly Met Met Phe Arg Gly Ile Ala Leu Ile His Val Pro Thr
            115                 120                 125

Thr Phe Leu Ala Ala Ser Asp Ser Val Leu Ser Ile Lys Gln Ala Val
        130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ala Glu Ser Pro Pro Arg Gln
                165                 170                 175

Val Lys Ala Gly Met Cys Glu Leu Val Lys Asn Met Leu Ile Leu Glu
                180                 185                 190

Asn Glu His Met Glu Phe Thr Glu Asp Leu Asn Ser Ala Asn Val
                195                 200                 205

Tyr Ser Pro Lys Gln Leu Glu Thr Phe Ile Asn Phe Cys Ile Ser Ala
            210                 215                 220

Lys Met Ser Val Leu Ser Glu Asp Ile Tyr Glu Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Val Ala Ile Ala Val Gly Met Ile Tyr
                260                 265                 270

Ala Ala Lys Ile Ala Asn Arg Met Asn Leu Leu Ser Glu Gln Asp Val
            275                 280                 285

Ser Thr His Tyr Trp Leu Leu Asn Lys Ile Gly Ala Leu Gln Glu Leu
        290                 295                 300

Pro Leu Arg Ala Asp Ala Asp Ser Val Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Glu Gly Ile Gly Arg Pro Ala Val His Asn Gln Ser Leu Leu
            340                 345                 350

Thr Pro Val Lys Lys Ser Leu Ile Lys Glu Val Ile Arg Glu Gly Leu
        355                 360                 365

```
<210> SEQ ID NO 7
<211> LENGTH: 1107
<212> TYPE: DNA
<213> ORGANISM: Paenibacillus sp.
<220> FEATURE:
<221> NAME/KEY: CDS
<222> LOCATION: (1)..(1107)

<400> SEQUENCE: 7 atg acg act aaa caa att tgt ttt gcg gac cgg tgt ttt aac ttt gca      48
Met Thr Thr Lys Gln Ile Cys Phe Ala Asp Arg Cys Phe Asn Phe Ala
 1               5                  10                  15
```

```
ttc ggc gaa cat gtt ttg gaa tcg gtt gaa tcc tat att ccc cgg gat      96
Phe Gly Glu His Val Leu Glu Ser Val Glu Ser Tyr Ile Pro Arg Asp
             20                  25                  30 gaa ttc gat caa tat atc atg att tcg gac tcg ggg gta ccg gac tcg     144
Glu Phe Asp Gln Tyr Ile Met Ile Ser Asp Ser Gly Val Pro Asp Ser
         35                  40                  45 att gtt cat cat gcg gcc gaa tac ttc ggc aga ctc gcc cct gta cat     192
Ile Val His His Ala Ala Glu Tyr Phe Gly Arg Leu Ala Pro Val His
     50                  55                  60 att ctt cgc ttt cag ggc gga gaa gaa tac aaa aca ctt gca acc gtg     240
Ile Leu Arg Phe Gln Gly Gly Glu Glu Tyr Lys Thr Leu Ala Thr Val
65                  70                  75                  80 aca aat ttg caa gag cag gca att gct ctg gga gcc aac cga aga acc     288
Thr Asn Leu Gln Glu Gln Ala Ile Ala Leu Gly Ala Asn Arg Arg Thr
                 85                  90                  95 gct atc gta gcg gtt ggc gga ggg tta acc gga aac gtt gcc gga gtg     336
Ala Ile Val Ala Val Gly Gly Gly Leu Thr Gly Asn Val Ala Gly Val
            100                 105                 110 gcg gcc ggc atg atg ttt cgc ggg att gcg ctt att cac gtt ccg acc     384
Ala Ala Gly Met Met Phe Arg Gly Ile Ala Leu Ile His Val Pro Thr
        115                 120                 125 acg ttt ttg gcg gcc tcc gat tcg gtt ctt tcg att aag cag gct gtt     432
Thr Phe Leu Ala Ala Ser Asp Ser Val Leu Ser Ile Lys Gln Ala Val
    130                 135                 140 aat tta acg agc gga aag aac ctg gtc ggc ttt tat tat ccg cca cgc     480
Asn Leu Thr Ser Gly Lys Asn Leu Val Gly Phe Tyr Tyr Pro Pro Arg
145                 150                 155                 160 ttc gtg ttc gcc gat acc cga atc ttg gcg gag tcg ccg ccc cgt cag     528
Phe Val Phe Ala Asp Thr Arg Ile Leu Ala Glu Ser Pro Pro Arg Gln
                165                 170                 175 gtg aaa gcg gga atg tgc gag ctg gta aaa aat atg ctg att ctg gaa     576
Val Lys Ala Gly Met Cys Glu Leu Val Lys Asn Met Leu Ile Leu Glu
            180                 185                 190 aac gag cac atg gaa ttt aca gag gat gat tta aat tca gcc aat gtg     624
Asn Glu His Met Glu Phe Thr Glu Asp Asp Leu Asn Ser Ala Asn Val
        195                 200                 205 tat tct ccg aag cag ctg gag acg ttt atc aac ttc tgc ata tcg gcc     672
Tyr Ser Pro Lys Gln Leu Glu Thr Phe Ile Asn Phe Cys Ile Ser Ala
    210                 215                 220 aaa atg tcg gta tta agc gaa gat att tac gag aaa aag aag ggc ctg     720
Lys Met Ser Val Leu Ser Glu Asp Ile Tyr Glu Lys Lys Lys Gly Leu
225                 230                 235                 240 atc ttt gag tac ggc cat acg atc ggt cat gcg atc gag ctt gcc gag     768
Ile Phe Glu Tyr Gly His Thr Ile Gly His Ala Ile Glu Leu Ala Glu
                245                 250                 255 cag gga ggg atc acg cac gga gaa gcc att gca gtg ggc atg att tac     816
Gln Gly Gly Ile Thr His Gly Glu Ala Ile Ala Val Gly Met Ile Tyr
            260                 265                 270 gcc gct aaa ata gcg aac cgg atg aac ctg atg ccc gaa cat gac gtg     864
Ala Ala Lys Ile Ala Asn Arg Met Asn Leu Met Pro Glu His Asp Val
        275                 280                 285 tcc gcc cat tac tgg ctt tta aat aaa atc ggg gcc ttg cag gag ctt     912
Ser Ala His Tyr Trp Leu Leu Asn Lys Ile Gly Ala Leu Gln Glu Leu
    290                 295                 300 ccg ctc cga gcg gac gcg gat tcg gtc ttc cat tat tta atc cac gat     960
Pro Leu Arg Ala Asp Ala Asp Ser Val Phe His Tyr Leu Ile His Asp
305                 310                 315                 320 aac aag agg ggc tac att aag ctg gat gag gat aat ttg ggt atg att    1008
Asn Lys Arg Gly Tyr Ile Lys Leu Asp Glu Asp Asn Leu Gly Met Ile
                325                 330                 335
```

```
tta ctt gag gga atc ggt cga ccg gcg gtt cat aac caa tcg ctg ctt      1056
Leu Leu Glu Gly Ile Gly Arg Pro Ala Val His Asn Gln Ser Leu Leu
        340                 345                 350 aca ccg gtc aag aaa tcg ctc ata aaa gaa gtg atc cgg gaa ggg ctg      1104
Thr Pro Val Lys Lys Ser Leu Ile Lys Glu Val Ile Arg Glu Gly Leu
        355                 360                 365 taa                                                                  1107

<210> SEQ ID NO 8
<211> LENGTH: 368
<212> TYPE: PRT
<213> ORGANISM: Paenibacillus sp.

<400> SEQUENCE: 8

Met Thr Thr Lys Gln Ile Cys Phe Ala Asp Arg Cys Phe Asn Phe Ala
1               5                   10                  15

Phe Gly Glu His Val Leu Glu Ser Val Glu Ser Tyr Ile Pro Arg Asp
            20                  25                  30

Glu Phe Asp Gln Tyr Ile Met Ile Ser Asp Ser Gly Val Pro Asp Ser
        35                  40                  45

Ile Val His His Ala Ala Glu Tyr Phe Gly Arg Leu Ala Pro Val His
    50                  55                  60

Ile Leu Arg Phe Gln Gly Gly Glu Tyr Lys Thr Leu Ala Thr Val
65                  70                  75                  80

Thr Asn Leu Gln Glu Gln Ala Ile Ala Leu Gly Ala Asn Arg Arg Thr
                85                  90                  95

Ala Ile Val Ala Val Gly Gly Leu Thr Gly Asn Val Ala Gly Val
            100                 105                 110

Ala Ala Gly Met Met Phe Arg Gly Ile Ala Leu Ile His Val Pro Thr
        115                 120                 125

Thr Phe Leu Ala Ala Ser Asp Ser Val Leu Ser Ile Lys Gln Ala Val
    130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ala Glu Ser Pro Pro Arg Gln
                165                 170                 175

Val Lys Ala Gly Met Cys Glu Leu Val Lys Asn Met Leu Ile Leu Glu
            180                 185                 190

Asn Glu His Met Glu Phe Thr Glu Asp Asp Leu Asn Ser Ala Asn Val
        195                 200                 205

Tyr Ser Pro Lys Gln Leu Glu Thr Phe Ile Asn Phe Cys Ile Ser Ala
    210                 215                 220

Lys Met Ser Val Leu Ser Glu Asp Ile Tyr Glu Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
            260                 265                 270

Ala Ala Lys Ile Ala Asn Arg Met Asn Leu Met Pro Glu His Asp Val
        275                 280                 285

Ser Ala His Tyr Trp Leu Leu Asn Lys Ile Gly Ala Leu Gln Glu Leu
    290                 295                 300

Pro Leu Arg Ala Asp Ala Asp Ser Val Phe His Tyr Leu Ile His Asp
305                 310                 315                 320

Asn Lys Arg Gly Tyr Ile Lys Leu Asp Glu Asp Asn Leu Gly Met Ile
                325                 330                 335
```

```
Leu Leu Glu Gly Ile Gly Arg Pro Ala Val His Asn Gln Ser Leu Leu
            340                 345                 350

Thr Pro Val Lys Lys Ser Leu Ile Lys Glu Val Ile Arg Glu Gly Leu
            355                 360                 365

<210> SEQ ID NO 9
<211> LENGTH: 1107
<212> TYPE: DNA
<213> ORGANISM: Paenibacillus sp.
<220> FEATURE:
<221> NAME/KEY: CDS
<222> LOCATION: (1)..(1107)

<400> SEQUENCE: 9
```

| | | | | | | | | | | | | | | | | |
|---|---|---|---|---|---|---|---|---|---|---|---|---|---|---|---|---|
| atg | acg | act | aaa | caa | att | tgt | ttt | gcg | gac | cgg | tgt | ttt | aac | ttt | gca | 48 |
| Met | Thr | Thr | Lys | Gln | Ile | Cys | Phe | Ala | Asp | Arg | Cys | Phe | Asn | Phe | Ala | |
| 1 | | | | 5 | | | | | 10 | | | | | 15 | | |
| ttc | ggc | gaa | cat | gtt | ttg | gaa | tcg | gtt | gaa | tcc | tat | att | ccc | cgg | gat | 96 |
| Phe | Gly | Glu | His | Val | Leu | Glu | Ser | Val | Glu | Ser | Tyr | Ile | Pro | Arg | Asp | |
| | | | 20 | | | | | 25 | | | | | 30 | | | |
| gaa | ttc | gat | caa | tat | atc | atg | att | tcg | gac | tcg | ggg | gta | ccg | gac | tcg | 144 |
| Glu | Phe | Asp | Gln | Tyr | Ile | Met | Ile | Ser | Asp | Ser | Gly | Val | Pro | Asp | Ser | |
| | | 35 | | | | | 40 | | | | | 45 | | | | |
| att | gtt | cat | tat | gcg | gcc | gaa | tac | ttc | ggc | aaa | ctc | gcc | cct | gta | cat | 192 |
| Ile | Val | His | Tyr | Ala | Ala | Glu | Tyr | Phe | Gly | Lys | Leu | Ala | Pro | Val | His | |
| 50 | | | | | 55 | | | | | 60 | | | | | | |
| att | ctt | cgc | ttt | cag | ggc | gga | gaa | gaa | tac | aaa | aca | ctt | gca | acc | gtg | 240 |
| Ile | Leu | Arg | Phe | Gln | Gly | Gly | Glu | Glu | Tyr | Lys | Thr | Leu | Ala | Thr | Val | |
| 65 | | | | | 70 | | | | | 75 | | | | | 80 | |
| aca | aat | ttg | caa | gag | cag | gca | att | gct | ctg | gga | gcc | aac | cga | aga | acc | 288 |
| Thr | Asn | Leu | Gln | Glu | Gln | Ala | Ile | Ala | Leu | Gly | Ala | Asn | Arg | Arg | Thr | |
| | | | | 85 | | | | | 90 | | | | | 95 | | |
| gct | atc | gta | gcg | gtt | ggc | gga | ggg | tta | acc | gga | aac | gtt | gcc | gga | gtg | 336 |
| Ala | Ile | Val | Ala | Val | Gly | Gly | Gly | Leu | Thr | Gly | Asn | Val | Ala | Gly | Val | |
| | | | 100 | | | | | 105 | | | | | 110 | | | |
| gcg | gcc | ggc | atg | atg | ttt | cgc | ggg | att | gcg | ctt | att | cac | gtt | ccg | acc | 384 |
| Ala | Ala | Gly | Met | Met | Phe | Arg | Gly | Ile | Ala | Leu | Ile | His | Val | Pro | Thr | |
| | | 115 | | | | | 120 | | | | | 125 | | | | |
| acg | ttt | ttg | gcg | gcc | tcc | gat | tcg | gtt | ctt | tcg | att | aag | cag | gct | gtt | 432 |
| Thr | Phe | Leu | Ala | Ala | Ser | Asp | Ser | Val | Leu | Ser | Ile | Lys | Gln | Ala | Val | |
| 130 | | | | | 135 | | | | | 140 | | | | | | |
| aat | tta | acg | agc | gga | aag | aac | ctg | gtc | ggc | ttt | tat | tat | ccg | cca | cgc | 480 |
| Asn | Leu | Thr | Ser | Gly | Lys | Asn | Leu | Val | Gly | Phe | Tyr | Tyr | Pro | Pro | Arg | |
| 145 | | | | | 150 | | | | | 155 | | | | | 160 | |
| ttc | gtg | ttc | gcc | gat | acc | cga | atc | ttg | gcg | gag | tcg | ccg | ccc | cgt | cag | 528 |
| Phe | Val | Phe | Ala | Asp | Thr | Arg | Ile | Leu | Ala | Glu | Ser | Pro | Pro | Arg | Gln | |
| | | | | 165 | | | | | 170 | | | | | 175 | | |
| gtg | aaa | gcg | gga | atg | tgc | gag | ctg | gta | aaa | aat | atg | ctg | att | ctg | gaa | 576 |
| Val | Lys | Ala | Gly | Met | Cys | Glu | Leu | Val | Lys | Asn | Met | Leu | Ile | Leu | Glu | |
| | | | 180 | | | | | 185 | | | | | 190 | | | |
| aac | gag | cac | atg | gaa | ttt | aca | gag | gat | gat | tta | aat | tca | gcc | aat | gtg | 624 |
| Asn | Glu | His | Met | Glu | Phe | Thr | Glu | Asp | Asp | Leu | Asn | Ser | Ala | Asn | Val | |
| | | 195 | | | | | 200 | | | | | 205 | | | | |
| tat | tct | ccg | aag | cag | ctg | gag | acg | ttt | atc | aac | ttc | tgc | ata | tcg | gcc | 672 |
| Tyr | Ser | Pro | Lys | Gln | Leu | Glu | Thr | Phe | Ile | Asn | Phe | Cys | Ile | Ser | Ala | |
| | | 210 | | | | | 215 | | | | | 220 | | | | |
| aaa | atg | tcg | gta | tta | agc | gaa | gat | att | tac | gag | aaa | aag | aag | ggc | ctg | 720 |
| Lys | Met | Ser | Val | Leu | Ser | Glu | Asp | Ile | Tyr | Glu | Lys | Lys | Lys | Gly | Leu | |
| 225 | | | | | 230 | | | | | 235 | | | | | 240 | |
| atc | ttt | gag | tac | ggc | cat | acg | atc | ggt | cat | gcg | atc | gag | ctt | gcc | gag | 768 |
| Ile | Phe | Glu | Tyr | Gly | His | Thr | Ile | Gly | His | Ala | Ile | Glu | Leu | Ala | Glu | |

```
                    245                 250                 255
cag gga ggg atc acg cac gga gaa gcc att gca gtg ggc atg att tac       816
Gln Gly Gly Ile Thr His Gly Glu Ala Ile Ala Val Gly Met Ile Tyr
                260                 265                 270 gcc gct aaa ata gcg aac cgg atg aac ctg atg ccc gaa cat gac gtg       864
Ala Ala Lys Ile Ala Asn Arg Met Asn Leu Met Pro Glu His Asp Val
            275                 280                 285 tcc gcc cat tac tgg ctt tta aat aaa atc ggg gcc ttg cag gat att       912
Ser Ala His Tyr Trp Leu Leu Asn Lys Ile Gly Ala Leu Gln Asp Ile
        290                 295                 300 ccg ctc aaa tcg gac ccg gat tcg atc ttc cat tat tta atc cac gat       960
Pro Leu Lys Ser Asp Pro Asp Ser Ile Phe His Tyr Leu Ile His Asp
305                 310                 315                 320 aac aag agg ggc tac att aag ctg gat gag gat aat ttg ggt atg att      1008
Asn Lys Arg Gly Tyr Ile Lys Leu Asp Glu Asp Asn Leu Gly Met Ile
                325                 330                 335 tta ctt gag gga atc ggt cga ccg gcg gtt cat aac caa tcg ctg ctt      1056
Leu Leu Glu Gly Ile Gly Arg Pro Ala Val His Asn Gln Ser Leu Leu
            340                 345                 350 aca ccg gtc aag aaa tcg ctc ata aaa gaa gtg atc cgg gaa ggg ctg      1104
Thr Pro Val Lys Lys Ser Leu Ile Lys Glu Val Ile Arg Glu Gly Leu
        355                 360                 365 taa                                                                  1107

<210> SEQ ID NO 10
<211> LENGTH: 368
<212> TYPE: PRT
<213> ORGANISM: Paenibacillus sp.

<400> SEQUENCE: 10

Met Thr Thr Lys Gln Ile Cys Phe Ala Asp Arg Cys Phe Asn Phe Ala
1               5                   10                  15

Phe Gly Glu His Val Leu Glu Ser Val Glu Ser Tyr Ile Pro Arg Asp
                20                  25                  30

Glu Phe Asp Gln Tyr Ile Met Ile Ser Asp Ser Gly Val Pro Asp Ser
            35                  40                  45

Ile Val His Tyr Ala Ala Glu Tyr Phe Gly Lys Leu Ala Pro Val His
        50                  55                  60

Ile Leu Arg Phe Gln Gly Gly Glu Glu Tyr Lys Thr Leu Ala Thr Val
65                  70                  75                  80

Thr Asn Leu Gln Glu Gln Ala Ile Ala Leu Gly Ala Asn Arg Arg Thr
                85                  90                  95

Ala Ile Val Ala Val Gly Gly Gly Leu Thr Gly Asn Val Ala Gly Val
            100                 105                 110

Ala Ala Gly Met Met Phe Arg Gly Ile Ala Leu Ile His Val Pro Thr
        115                 120                 125

Thr Phe Leu Ala Ala Ser Asp Ser Val Leu Ser Ile Lys Gln Ala Val
130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ala Glu Ser Pro Pro Arg Gln
                165                 170                 175

Val Lys Ala Gly Met Cys Glu Leu Val Lys Asn Met Leu Ile Leu Glu
            180                 185                 190

Asn Glu His Met Glu Phe Thr Glu Asp Asp Leu Asn Ser Ala Asn Val
        195                 200                 205

Tyr Ser Pro Lys Gln Leu Glu Thr Phe Ile Asn Phe Cys Ile Ser Ala
```

```
                 210                 215                 220
Lys Met Ser Val Leu Ser Glu Asp Ile Tyr Glu Lys Lys Gly Leu
225                 230                 235                 240

Ile Phe Glu Tyr Gly His Thr Ile Gly His Ala Ile Glu Leu Ala Glu
                245                 250                     255

Gln Gly Gly Ile Thr His Gly Glu Ala Ile Ala Val Gly Met Ile Tyr
                    260                 265                 270

Ala Ala Lys Ile Ala Asn Arg Met Asn Leu Met Pro Glu His Asp Val
                275                 280                 285

Ser Ala His Tyr Trp Leu Leu Asn Lys Ile Gly Ala Leu Gln Asp Ile
                290                 295                 300

Pro Leu Lys Ser Asp Pro Asp Ser Ile Phe His Tyr Leu Ile His Asp
305                 310                 315                 320

Asn Lys Arg Gly Tyr Ile Lys Leu Asp Glu Asp Asn Leu Gly Met Ile
                    325                 330                 335

Leu Leu Glu Gly Ile Gly Arg Pro Ala Val His Asn Gln Ser Leu Leu
                340                 345                 350

Thr Pro Val Lys Lys Ser Leu Ile Lys Glu Val Ile Arg Glu Gly Leu
                355                 360                 365

<210> SEQ ID NO 11
<211> LENGTH: 1107
<212> TYPE: DNA
<213> ORGANISM: Paenibacillus sp.
<220> FEATURE:
<221> NAME/KEY: CDS
<222> LOCATION: (1)..(1107)

<400> SEQUENCE: 11 atg acg act aaa caa att tgt ttt gcg gac cgg tgt ttt aac ttt gca      48
Met Thr Thr Lys Gln Ile Cys Phe Ala Asp Arg Cys Phe Asn Phe Ala
1               5                   10                  15 ttc ggc gaa cat gtt ttg gaa tcg gtt gaa tcc tat att ccc cgg gat      96
Phe Gly Glu His Val Leu Glu Ser Val Glu Ser Tyr Ile Pro Arg Asp
                20                  25                  30 gaa ttc gat caa tat atc atg att tcg gac tcg ggg gta ccg gac tcg     144
Glu Phe Asp Gln Tyr Ile Met Ile Ser Asp Ser Gly Val Pro Asp Ser
            35                  40                  45 att gtt cat tat gcg gcc gaa tac ttc ggc aaa ctc gcc cct gta cat     192
Ile Val His Tyr Ala Ala Glu Tyr Phe Gly Lys Leu Ala Pro Val His
        50                  55                  60 att ctt cgc ttt cag ggc gga gaa gaa tac aaa aca ctt tca acc gtg     240
Ile Leu Arg Phe Gln Gly Gly Glu Glu Tyr Lys Thr Leu Ser Thr Val
65                  70                  75                  80 aca aat ttg caa gag cgg gca att gct ctg gga gcc aac cga aga acc     288
Thr Asn Leu Gln Glu Arg Ala Ile Ala Leu Gly Ala Asn Arg Arg Thr
                85                  90                  95 gct atc gta gcg gtt ggc gga ggg tta acc gga aac gtt gcc gga gtg     336
Ala Ile Val Ala Val Gly Gly Gly Leu Thr Gly Asn Val Ala Gly Val
            100                 105                 110 gcg gcc ggc atg atg ttt cgc ggg att gcg ctt att cac gtt ccg acc     384
Ala Ala Gly Met Met Phe Arg Gly Ile Ala Leu Ile His Val Pro Thr
        115                 120                 125 acg ttt ttg gcg gcc tcc gat tcg gtt ctt tcg att aag cag gct gtt     432
Thr Phe Leu Ala Ala Ser Asp Ser Val Leu Ser Ile Lys Gln Ala Val
    130                 135                 140 aat tta acg agc gga aag aac ctg gtc ggc ttt tat tat ccg cca cgc     480
Asn Leu Thr Ser Gly Lys Asn Leu Val Gly Phe Tyr Tyr Pro Pro Arg
145                 150                 155                 160
```

-continued

```
ttc gtg ttc gcc gat acc cga atc ttg tcg gag tcg ccg ccc cgt cag     528
Phe Val Phe Ala Asp Thr Arg Ile Leu Ser Glu Ser Pro Pro Arg Gln
            165                 170                 175 gtg aaa gcg gga atg tgc gag ctg gta aaa aat atg ctg att ctg gaa     576
Val Lys Ala Gly Met Cys Glu Leu Val Lys Asn Met Leu Ile Leu Glu
        180                 185                 190 aac gag cac atg gaa ttt aca gag gat gat tta aat tca gcc aat gtg     624
Asn Glu His Met Glu Phe Thr Glu Asp Asp Leu Asn Ser Ala Asn Val
    195                 200                 205 tat tct ccg aag cag ctg gag acg ttt atc aac ttc tgc ata tcg gcc     672
Tyr Ser Pro Lys Gln Leu Glu Thr Phe Ile Asn Phe Cys Ile Ser Ala
210                 215                 220 aaa atg tcg gta tta agc gaa gat att tac gag aaa aag aag ggc ctg     720
Lys Met Ser Val Leu Ser Glu Asp Ile Tyr Glu Lys Lys Lys Gly Leu
225                 230                 235                 240 atc ttt gag tac ggc cat acg atc ggt cat gcg atc gag ctt gcc gag     768
Ile Phe Glu Tyr Gly His Thr Ile Gly His Ala Ile Glu Leu Ala Glu
            245                 250                 255 cag gga ggg atc acg cac gga gaa gcc att gca gtg ggc atg att tac     816
Gln Gly Gly Ile Thr His Gly Glu Ala Ile Ala Val Gly Met Ile Tyr
        260                 265                 270 gcc gct aaa ata gcg aac cgg atg aac ctg atg ccc gaa cat gac gtg     864
Ala Ala Lys Ile Ala Asn Arg Met Asn Leu Met Pro Glu His Asp Val
    275                 280                 285 tcc gcc cat tac tgg ctt tta aat aaa atc ggg gcc ttg cag gat att     912
Ser Ala His Tyr Trp Leu Leu Asn Lys Ile Gly Ala Leu Gln Asp Ile
290                 295                 300 ccg ctc aaa tcg gac ccg gat tcg atc ttc cat tat tta atc cac gat     960
Pro Leu Lys Ser Asp Pro Asp Ser Ile Phe His Tyr Leu Ile His Asp
305                 310                 315                 320 aac aag agg ggc tac att aag ctg gat gag gat aat ttg ggt atg att    1008
Asn Lys Arg Gly Tyr Ile Lys Leu Asp Glu Asp Asn Leu Gly Met Ile
            325                 330                 335 tta ctt agc gga gtc ggt aaa ccg gcg atg tat aac caa acg ctg ctt    1056
Leu Leu Ser Gly Val Gly Lys Pro Ala Met Tyr Asn Gln Thr Leu Leu
        340                 345                 350 aca ccg gtc aga aaa acg ctc ata aaa gaa gtg atc cgg gaa ggg ctg    1104
Thr Pro Val Arg Lys Thr Leu Ile Lys Glu Val Ile Arg Glu Gly Leu
    355                 360                 365 taa                                                                1107
```

<210> SEQ ID NO 12
<211> LENGTH: 368
<212> TYPE: PRT
<213> ORGANISM: Paenibacillus sp.

<400> SEQUENCE: 12

```
Met Thr Thr Lys Gln Ile Cys Phe Ala Asp Arg Cys Phe Asn Phe Ala
1               5                   10                  15

Phe Gly Glu His Val Leu Glu Ser Val Glu Ser Tyr Ile Pro Arg Asp
            20                  25                  30

Glu Phe Asp Gln Tyr Ile Met Ile Ser Asp Ser Gly Val Pro Asp Ser
        35                  40                  45

Ile Val His Tyr Ala Ala Glu Tyr Phe Gly Lys Leu Ala Pro Val His
    50                  55                  60

Ile Leu Arg Phe Gln Gly Gly Glu Glu Tyr Lys Thr Leu Ser Thr Val
65                  70                  75                  80

Thr Asn Leu Gln Glu Arg Ala Ile Ala Leu Gly Ala Asn Arg Arg Thr
            85                  90                  95
```

```
Ala Ile Val Ala Val Gly Gly Leu Thr Gly Asn Val Ala Gly Val
                100                 105                 110

Ala Ala Gly Met Met Phe Arg Gly Ile Ala Leu Ile His Val Pro Thr
            115                 120                 125

Thr Phe Leu Ala Ala Ser Asp Ser Val Leu Ser Ile Lys Gln Ala Val
130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ser Glu Ser Pro Pro Arg Gln
                165                 170                 175

Val Lys Ala Gly Met Cys Glu Leu Val Lys Asn Met Leu Ile Leu Glu
            180                 185                 190

Asn Glu His Met Glu Phe Thr Glu Asp Asp Leu Asn Ser Ala Asn Val
        195                 200                 205

Tyr Ser Pro Lys Gln Leu Glu Thr Phe Ile Asn Phe Cys Ile Ser Ala
    210                 215                 220

Lys Met Ser Val Leu Ser Glu Asp Ile Tyr Glu Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
            260                 265                 270

Ala Ala Lys Ile Ala Asn Arg Met Asn Leu Met Pro Glu His Asp Val
        275                 280                 285

Ser Ala His Tyr Trp Leu Leu Asn Lys Ile Gly Ala Leu Gln Asp Ile
    290                 295                 300

Pro Leu Lys Ser Asp Pro Asp Ser Ile Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Ser Gly Val Gly Lys Pro Ala Met Tyr Asn Gln Thr Leu Leu
            340                 345                 350

Thr Pro Val Arg Lys Thr Leu Ile Lys Glu Val Ile Arg Glu Gly Leu
        355                 360                 365

<210> SEQ ID NO 13
<211> LENGTH: 1107
<212> TYPE: DNA
<213> ORGANISM: Paenibacillus sp.
<220> FEATURE:
<221> NAME/KEY: CDS
<222> LOCATION: (1)..(1107)

<400> SEQUENCE: 13 atg acg act aaa caa att tgt ttt gcg gac cgg tgt ttt aac ttt gca    48
Met Thr Thr Lys Gln Ile Cys Phe Ala Asp Arg Cys Phe Asn Phe Ala
1               5                   10                  15 ttc ggc gaa cat gtt ttg gaa tcg gtt gaa tcc tat att ccc cgg gat    96
Phe Gly Glu His Val Leu Glu Ser Val Glu Ser Tyr Ile Pro Arg Asp
                20                  25                  30 gaa ttc gat caa tat atc atg att tcg gac tcg ggg gta ccg gac tcg   144
Glu Phe Asp Gln Tyr Ile Met Ile Ser Asp Ser Gly Val Pro Asp Ser
            35                  40                  45 att gtt cat tat gcg gcc gaa tac ttc ggc aaa ctc gcc cct gta cat   192
Ile Val His Tyr Ala Ala Glu Tyr Phe Gly Lys Leu Ala Pro Val His
        50                  55                  60 att ctt cgc ttt cag ggc gga gaa gaa tac aaa aca ctt tca acc gtg   240
Ile Leu Arg Phe Gln Gly Gly Glu Glu Tyr Lys Thr Leu Ser Thr Val
```

|  |  |  |  |  |  |  |  |  |  |  |  |  |  |  |  |  |
|---|---|---|---|---|---|---|---|---|---|---|---|---|---|---|---|---|
| | | 65 | | | | 70 | | | | 75 | | | | 80 | | |
| aca | aat | ttg | caa | gag | cgg | gca | att | gct | ctg | gga | gcc | aac | cga | aga | acc | 288 |
| Thr | Asn | Leu | Gln | Glu | Arg | Ala | Ile | Ala | Leu | Gly | Ala | Asn | Arg | Arg | Thr | |
| | | | | 85 | | | | | 90 | | | | | 95 | | |
| gct | atc | gta | gcg | gtt | ggc | gga | ggg | tta | acc | gga | aac | gtt | gcc | gga | gtg | 336 |
| Ala | Ile | Val | Ala | Val | Gly | Gly | Gly | Leu | Thr | Gly | Asn | Val | Ala | Gly | Val | |
| | | 100 | | | | | 105 | | | | | 110 | | | | |
| gcg | gcc | ggc | atg | atg | ttt | cgc | ggg | att | gcg | ctt | att | cac | gtt | ccg | acc | 384 |
| Ala | Ala | Gly | Met | Met | Phe | Arg | Gly | Ile | Ala | Leu | Ile | His | Val | Pro | Thr | |
| | | 115 | | | | | 120 | | | | | 125 | | | | |
| acg | ttt | ttg | gcg | gcc | tcc | gat | tcg | gtt | ctt | tcg | att | aag | cag | gct | gtt | 432 |
| Thr | Phe | Leu | Ala | Ala | Ser | Asp | Ser | Val | Leu | Ser | Ile | Lys | Gln | Ala | Val | |
| | 130 | | | | | 135 | | | | | 140 | | | | | |
| aat | tta | acg | agc | gga | aag | aac | ctg | gtc | ggc | ttt | tat | tat | ccg | cca | cgc | 480 |
| Asn | Leu | Thr | Ser | Gly | Lys | Asn | Leu | Val | Gly | Phe | Tyr | Tyr | Pro | Pro | Arg | |
| 145 | | | | | 150 | | | | | 155 | | | | | 160 | |
| ttc | gtg | ttc | gcc | gat | acc | cga | atc | ttg | tcg | gag | tcg | ccg | ccc | cgt | cag | 528 |
| Phe | Val | Phe | Ala | Asp | Thr | Arg | Ile | Leu | Ser | Glu | Ser | Pro | Pro | Arg | Gln | |
| | | | | 165 | | | | | 170 | | | | | 175 | | |
| gtg | aaa | gcg | gga | atg | tgc | gag | ctg | gta | aaa | aat | atg | ctg | att | ctg | gaa | 576 |
| Val | Lys | Ala | Gly | Met | Cys | Glu | Leu | Val | Lys | Asn | Met | Leu | Ile | Leu | Glu | |
| | | | 180 | | | | | 185 | | | | | 190 | | | |
| aac | gac | aac | aag | gaa | ttt | aca | gag | gat | gat | tta | aat | tca | gcc | aat | gtg | 624 |
| Asn | Asp | Asn | Lys | Glu | Phe | Thr | Glu | Asp | Asp | Leu | Asn | Ser | Ala | Asn | Val | |
| | | 195 | | | | | 200 | | | | | 205 | | | | |
| tat | tct | ccg | aag | cag | ctg | gag | acg | ttt | atc | aac | ttc | tgc | ata | tcg | gcc | 672 |
| Tyr | Ser | Pro | Lys | Gln | Leu | Glu | Thr | Phe | Ile | Asn | Phe | Cys | Ile | Ser | Ala | |
| | 210 | | | | | 215 | | | | | 220 | | | | | |
| aaa | atg | tcg | gta | tta | agc | gaa | gat | att | tac | gag | aaa | aag | aag | ggc | ctg | 720 |
| Lys | Met | Ser | Val | Leu | Ser | Glu | Asp | Ile | Tyr | Glu | Lys | Lys | Lys | Gly | Leu | |
| 225 | | | | | 230 | | | | | 235 | | | | | 240 | |
| atc | ttt | gag | tac | ggc | cat | acg | atc | ggt | cat | gcg | atc | gag | ctt | gcc | gag | 768 |
| Ile | Phe | Glu | Tyr | Gly | His | Thr | Ile | Gly | His | Ala | Ile | Glu | Leu | Ala | Glu | |
| | | | | 245 | | | | | 250 | | | | | 255 | | |
| cag | gga | ggg | atc | acg | cac | gga | gaa | gcc | att | gca | gtg | ggc | atg | att | tac | 816 |
| Gln | Gly | Gly | Ile | Thr | His | Gly | Glu | Ala | Ile | Ala | Val | Gly | Met | Ile | Tyr | |
| | | | 260 | | | | | 265 | | | | | 270 | | | |
| gcc | gct | aaa | ata | gcg | aac | cgg | atg | aac | ctg | atg | ccc | gaa | cat | gac | gtg | 864 |
| Ala | Ala | Lys | Ile | Ala | Asn | Arg | Met | Asn | Leu | Met | Pro | Glu | His | Asp | Val | |
| | | 275 | | | | | 280 | | | | | 285 | | | | |
| tcc | gcc | cat | tac | tgg | ctt | tta | aat | aaa | atc | ggg | gcc | ttg | cag | gat | att | 912 |
| Ser | Ala | His | Tyr | Trp | Leu | Leu | Asn | Lys | Ile | Gly | Ala | Leu | Gln | Asp | Ile | |
| | 290 | | | | | 295 | | | | | 300 | | | | | |
| ccg | ctc | aaa | tcg | gac | ccg | gat | tcg | atc | ttc | cat | tat | tta | atc | cac | gat | 960 |
| Pro | Leu | Lys | Ser | Asp | Pro | Asp | Ser | Ile | Phe | His | Tyr | Leu | Ile | His | Asp | |
| 305 | | | | | 310 | | | | | 315 | | | | | 320 | |
| aac | aag | agg | ggc | tac | att | aag | ctg | gat | gag | gat | aat | ttg | ggt | atg | att | 1008 |
| Asn | Lys | Arg | Gly | Tyr | Ile | Lys | Leu | Asp | Glu | Asp | Asn | Leu | Gly | Met | Ile | |
| | | | | 325 | | | | | 330 | | | | | 335 | | |
| tta | ctt | agc | gga | gtc | ggt | aaa | ccg | gcg | atg | tat | aac | caa | acg | ctg | ctt | 1056 |
| Leu | Leu | Ser | Gly | Val | Gly | Lys | Pro | Ala | Met | Tyr | Asn | Gln | Thr | Leu | Leu | |
| | | | 340 | | | | | 345 | | | | | 350 | | | |
| aca | ccg | gtc | aga | aaa | acg | ctc | ata | aaa | gaa | gtg | atc | cgg | gaa | ggg | ctg | 1104 |
| Thr | Pro | Val | Arg | Lys | Thr | Leu | Ile | Lys | Glu | Val | Ile | Arg | Glu | Gly | Leu | |
| | | 355 | | | | | 360 | | | | | 365 | | | | |
| taa | | | | | | | | | | | | | | | | 1107 |

<210> SEQ ID NO 14
<211> LENGTH: 368
<212> TYPE: PRT

<213> ORGANISM: Paenibacillus sp.

<400> SEQUENCE: 14

Met Thr Thr Lys Gln Ile Cys Phe Ala Asp Arg Cys Phe Asn Phe Ala
1               5                   10                  15

Phe Gly Glu His Val Leu Glu Ser Val Glu Ser Tyr Ile Pro Arg Asp
            20                  25                  30

Glu Phe Asp Gln Tyr Ile Met Ile Ser Asp Ser Gly Val Pro Asp Ser
        35                  40                  45

Ile Val His Tyr Ala Ala Glu Tyr Phe Gly Lys Leu Ala Pro Val His
    50                  55                  60

Ile Leu Arg Phe Gln Gly Gly Glu Glu Tyr Lys Thr Leu Ser Thr Val
65                  70                  75                  80

Thr Asn Leu Gln Glu Arg Ala Ile Ala Leu Gly Ala Asn Arg Arg Thr
                85                  90                  95

Ala Ile Val Ala Val Gly Gly Leu Thr Gly Asn Val Ala Gly Val
            100                 105                 110

Ala Ala Gly Met Met Phe Arg Gly Ile Ala Leu Ile His Val Pro Thr
        115                 120                 125

Thr Phe Leu Ala Ala Ser Asp Ser Val Leu Ser Ile Lys Gln Ala Val
    130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ser Glu Ser Pro Pro Arg Gln
                165                 170                 175

Val Lys Ala Gly Met Cys Glu Leu Val Lys Asn Met Leu Ile Leu Glu
            180                 185                 190

Asn Asp Asn Lys Glu Phe Thr Glu Asp Leu Asn Ser Ala Asn Val
        195                 200                 205

Tyr Ser Pro Lys Gln Leu Glu Thr Phe Ile Asn Phe Cys Ile Ser Ala
    210                 215                 220

Lys Met Ser Val Leu Ser Glu Asp Ile Tyr Glu Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
            260                 265                 270

Ala Ala Lys Ile Ala Asn Arg Met Asn Leu Met Pro Glu His Asp Val
        275                 280                 285

Ser Ala His Tyr Trp Leu Leu Asn Lys Ile Gly Ala Leu Gln Asp Ile
    290                 295                 300

Pro Leu Lys Ser Asp Pro Asp Ser Ile Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Ser Gly Val Gly Lys Pro Ala Met Tyr Asn Gln Thr Leu Leu
            340                 345                 350

Thr Pro Val Arg Lys Thr Leu Ile Lys Glu Val Ile Arg Glu Gly Leu
        355                 360                 365

<210> SEQ ID NO 15
<211> LENGTH: 26
<212> TYPE: DNA
<213> ORGANISM: Artificial Sequence
<220> FEATURE:
<223> OTHER INFORMATION: Synthetic primer

```
<400> SEQUENCE: 15
atgacgacta aacaaatttg ttttgc                                              26

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
ttacagccct tcccggatc                                                      19
```

2-DEOXY-SCYLLO-INOSOSE SYNTHASE

RELATED APPLICATIONS

The present application is a U.S. National Phase Application of International Application No. PCT/JP2010/002210 (filed Mar. 26, 2010) which claims priority to Japanese Application No. 2009-075802 (filed Mar. 26, 2009); Japanese Application No. 2009-075803 (filed Mar. 26, 2009); Japanese Application No. 2009-075804 (filed Mar. 26, 2009); Japanese Application No. 2009-075805 (filed Mar. 26, 2009); Japanese Application No. 2009-075806 (filed Mar. 26, 2009) and Japanese Application No. 2009-078713 (filed Mar. 27, 2009) which are hereby incorporated by reference in their entirety.

TECHNICAL FIELD

The present invention relates to a heat-resistant 2-deoxy-scyllo-inosose synthase, a 2-deoxy-scyllo-inosose synthase gene, a recombinant vector, a transformant, and a method for producing 2-deoxy-scyllo-inosose.

BACKGROUND ART

At present, a majority of aromatic compounds, such as catechol, are produced from petroleum as a raw material. From the viewpoint of the problem of depleted oil resources or reduction in the amount of carbon dioxide emissions, it is desired to develop a novel environment-conscious production process in which a biomass is used.

On the other hand, it has been found that 2-deoxy-scyllo-inosose (hereinafter referred to as DOI) can be converted to an industrially useful aromatic compound (e.g. catechol, etc.) (Non-Patent Document 1), and it has been reported that this DOI can be synthesized from glucose that is one constituent of biomass (Non-Patent Document 1). An enzyme that plays an important role in this process of producing DOI is a 2-deoxy-scyllo-inosose synthase (hereinafter referred to as a DOI synthase) for converting glucose-6-phosphate to DOI. Since the DOI is not only converted to the aforementioned aromatic compound but can also be an intermediate of various types of useful compounds, the DOI synthase has received a great deal of attention.

A DOI synthase has been isolated and purified from microorganisms belonging to Bacillus circulans that is a butirosin-producing bacterium in 1997 (Non-Patent Document 2), and the gene sequence thereof has been then published (Patent Document 1). Other than this DOI synthase, a DOI synthase derived from a Streptoalloteichus hindustanus JCM3268 strain (Non-Patent Document 3) and the like have been discovered so far.

PRIOR ART REFERENCES

Patent Documents

Patent Document 1: JP Patent Publication (Kokai) No. 2000-236881

Non-Patent Documents

Non-Patent Document 1: Tetrahedron Letters 41, 1935-1938, 2000

Non-Patent Document 2: The Journal of Antibiotics 50(5), 424-428, 1997

Non-Patent Document 3: The Journal of Antibiotics 59(6), 358-361, 2006

SUMMARY OF INVENTION

Object to be Solved by the Invention

However, various types of properties of the above-described DOI synthase, such as stability and specific activity, have not been satisfactory. In addition, the analysis of the enzyme directed towards the development of an industrial production method at a scale of several thousands of tons and studies regarding the improvement of functions have rarely been carried out. For example, the DOI synthase (BtrC) derived from microorganisms belonging to Bacillus circulans has a serious problem regarding stability and the like. Moreover, the DOI synthase derived from the Streptoalloteichus hindustanus JCM3268 strain has significantly low specific activity, and thus, the industrial application of this enzyme has been difficult. An object to be solved by the present invention is to provide a DOI synthase having properties such as stability to heat and pH, which are superior to those of conventional enzymes, and a method for producing DOI using the above-mentioned enzyme.

Means for Solving the Object

As a result of intensive studies directed towards achieving the aforementioned object, the present inventors have discovered a DOI synthase having heat stability and/or pH stability that are superior to those of conventional enzymes, thereby completing the present invention.

Specifically, the present invention relates to a DOI synthase, a DOI synthase gene, a recombinant vector, a transformant and a method for producing DOI, which will be described below.

[1] A 2-deoxy-scyllo-inosose synthase having the properties described in the following (1), (2), (4), (6) and (7), and also having the properties described in the following (3) and/or (5):
(1) action: the enzyme has a function to convert glucose-6-phosphate to 2-deoxy-scyllo-inosose;
(2) optimum pH range: pH 7.0 to 7.7;
(3) stable pH range: pH 6.0 to 8.0;
(4) optimum temperature range: 55° C. to 70° C.;
(5) stable temperature range: 20° C. to 46° C.;
(6) coenzyme used: $NAD^+$; and
(7) molecular weight: 39,000 to 42,000.
[2] The 2-deoxy-scyllo-inosose synthase according to [1] above, which has the property described in the following (8):
(8) specific activity: 1.0 μmol/min/mg or greater (reaction temperature: 65° C.).
[3] The 2-deoxy-scyllo-inosose synthase according to [1] or [2] above, which has the property described in the following (9):
(9) cofactor: activity being improved by addition of $Co^{2+}$ ion.
[4] The 2-deoxy-scyllo-inosose synthase according to any one of [1] to [3] above, wherein the stable temperature range is 20° C. to 60° C.
[5] A 2-deoxy-scyllo-inosose synthase having any one of the following amino acid sequences:
(a) the amino acid sequence shown in any one of SEQ ID NOS: 2, 4, 6, 8, 10 and 12;
(b) an amino acid sequence having homology of 80% or more with the amino acid sequence shown in any one of SEQ ID NOS: 2, 4, 6, 8, 10 and 12, and having high temperature stability and/or wide range pH stability; and (c) an amino acid sequence comprising a deletion, addition and/or substitution of one or multiple amino acids with respect to the amino acid sequence shown in any one of SEQ ID NOS: 2, 4, 6, 8, 10 and 12, and having high temperature stability and/or wide range pH stability.

[6] A 2-deoxy-scyllo-inosose synthase gene having a nucleotide sequence encoding any one of the following amino acid sequences:
(a) the amino acid sequence shown in any one of SEQ ID NOS: 2, 4, 6, 8, 10 and 12;
(b) an amino acid sequence having homology of 80% or more with the amino acid sequence shown in any one of SEQ ID NOS: 2, 4, 6, 8, 10 and 12, and having high temperature stability and/or wide range pH stability; and
(c) an amino acid sequence comprising a deletion, addition and/or substitution of one or multiple amino acids with respect to the amino acid sequence shown in any one of SEQ ID NOS: 2, 4, 6, 8, 10 and 12, and having high temperature stability and/or wide range pH stability.

[7] A 2-deoxy-scyllo-inosose synthase gene having any one of the following nucleotide sequences:
(a) the nucleotide sequence shown in any one of SEQ ID NOS: 1, 3, 5, 7, 9 and 11;
(b) a nucleotide sequence having homology of 80% or more with the nucleotide sequence shown in any one of SEQ ID NOS: 1, 3, 5, 7, 9 and 11, and encoding a 2-deoxy-scyllo-inosose synthase having high temperature stability and/or wide range pH stability; and
(c) a nucleotide sequence comprising a deletion, addition and/or substitution of one or multiple nucleotides with respect to the nucleotide sequence shown in any one of SEQ ID NOS: 1, 3, 5, 7, 9 and 11, and encoding a 2-deoxy-scyllo-inosose synthase having high temperature stability and/or wide range pH stability

[8] A recombinant vector which comprises the 2-deoxy-scyllo-inosose synthase gene according to [6] or [7] above.

[9] A transformant which is obtained by introducing the 2-deoxy-scyllo-inosose synthase gene according to [6] or [7] above or the recombinant vector according to [8] above into a host.

[10] A 2-deoxy-scyllo-inosose synthase which is obtained by culturing the transformant according to [9] above.

[11] A method for producing 2-deoxy-scyllo-inosose, wherein the 2-deoxy-scyllo-inosose synthase according to any one of [1] to [5] and [10] above is used.

[12] A method for producing 2-deoxy-scyllo-inosose, using, as a raw material, glucose, polysaccharide comprising glucose as a constituent, and/or glucose-6-phosphate, wherein the 2-deoxy-scyllo-inosose synthase gene according to [6] or [7] above or the transformant according to [9] above is utilized.

[13] A method for producing 2-deoxy-scyllo-inosose from glucose-6-phosphate, wherein a microorganism capable of expressing 2-deoxy-scyllo-inosose synthase is cultured in a medium containing a cobalt ion.

[14] The method according to [13] above, wherein a raw material that contains polysaccharide comprising glucose as a constituent, or glucose, is used

[15] The method according to [13] or [14] above, wherein the 2-deoxy-scyllo-inosose synthase is the 2-deoxy-scyllo-inosose synthase according to any one of [1] to [5] above.

Advantageous Effects of Invention

The DOI synthase of the present invention can be used under high temperature conditions in the production of DOI. Moreover, strict temperature control is not required during the production of DOI, depending on production conditions. Furthermore, the present DOI synthase enables the production of DOI under acidic conditions which is a pH range wherein DOI is stable. Further, strict pH control is not required during the production of DOI, depending on production conditions.

BRIEF DESCRIPTION OF DRAWINGS

FIG. 1 shows the optimum pH range of a purified DOI synthase (DOIS-1) (Example 3).

FIG. 2 shows the stable pH range of a purified DOI synthase (DOIS-1) (Example 3).

FIG. 3 shows the optimum temperature range of a purified DOI synthase (DOIS-1) (Example 3).

FIG. 4 shows the stable temperature range of a purified DOI synthase (DOIS-1) (Example 3).

FIG. 5 shows the stable temperature range of a purified DOI synthase (DOIS-5) (Example 5)

FIG. 6 shows the stable temperature range of a known purified DOI synthase (BtrC) (Comparative Example 1).

FIG. 7 shows the stable pH range of a known purified DOI synthase (BtrC) (Comparative Example 1).

EMBODIMENTS FOR CARRYING OUT THE INVENTION

The present invention will be specifically described below.
[DOI Synthase]
The DOI synthase in the embodiment for carrying out the present invention (hereinafter referred to as "the present embodiment") has the following properties:
(1) action: the present enzyme has a function to convert glucose-6-phosphate to DOI; and
(2) stability: the present enzyme shows high temperature stability and/or wide range pH stability.

Preferably, the DOI synthase according to the present invention has the properties described in the following (1), (2), (4), (6) and (7), and also having the properties described in the following (3) and/or (5):
(1) action: the present enzyme has a function to convert glucose-6-phosphate to 2-deoxy-scyllo-inosose;
(2) optimum pH range: pH 7.0 to 7.7;
(3) stable pH range: pH 6.0 to 8.0;
(4) optimum temperature range: 55° C. to 70° C.;
(5) stable temperature range: 20° C. to 46° C. (preferably 20° C. to 60° C.);
(6) coenzyme used: $NAD^+$; and
(7) molecular weight: 39,000 to 42,000.

More preferably, the DOI synthase according to the present invention has the properties described in the following (8) and/or (9), in addition to the above-described properties:
(8) specific activity: 1.0 µmol/min/mg or greater (reaction temperature: 65° C.); and
(9) cofactor: activity being improved by addition of $Co^{2+}$ ion.

Specific examples of the amino acid sequences of the DOI synthase of the present invention are shown in SEQ ID NOS: 2, 4, 6, 8, 10 and 12. The DOI synthase having the amino acid sequence shown in SEQ ID NO: 2, 4, 6, 8, 10 or 12 preferably has properties of high temperature stability and/or wide range pH stability. The DOI synthase having the amino acid sequence shown in SEQ ID NO: 2, 4, 6, 8, 10 or 12 preferably has excellent properties of high temperature stability and/or wide range pH stability in the present embodiment.

In the present embodiment, the DOI synthase may be a protein having homology of preferably 80% or more, more preferably 85% or more, further preferably 90% or more, still further preferably 95% or more, and still further preferably 99% or more, with at least one amino acid sequence selected from the group consisting of the amino acid sequences shown in SEQ ID NOS: 2, 4, 6, 8, 10 and 12.

Moreover, in the present embodiment, the DOI synthase may comprise a deletion, substitution and/or addition of one or multiple amino acids with respect to at least one amino acid sequence selected from the group consisting of the amino acid sequences shown in SEQ ID NOS: 2, 4, 6, 8, 10 and 12. The number of amino acids which are deleted, substituted and/or added is preferably 1 to 50, more preferably 1 to 30, further preferably 1 to 20, still further preferably 1 to 10, still further preferably 1 to 5, and still further preferably 1 to 3.

An enzyme, which has an amino acid sequence having homology of 80% or more with at least one amino acid sequence selected from the group consisting of the amino acid sequences shown in SEQ ID NOS: 2, 4, 6, 8, 10 and 12, which has excellent properties of high temperature stability and/or wide range pH stability, and which has DOI synthase activity, is included in the present invention.

An enzyme, which has an amino acid sequence comprising a deletion, substitution and/or addition of one or multiple amino acids with respect to at least one amino acid sequence selected from the group consisting of the amino acid sequences shown in SEQ ID NOS: 2, 4, 6, 8, 10 and 12, which has excellent properties of high temperature stability and/or wide range pH stability, and which has DOI synthase activity, is included in the present invention.

As a method of causing a mutation such as a deletion, substitution or addition to amino acids in a DOI synthase, there can be applied known methods such as a PCR method, an error-prone PCR method, a DNA shuffling method or a means for producing a chimeric enzyme.

The homology between the amino acid sequences of DOI synthases can be calculated using sequence analysis tools, such as a BESTFIT program provided by UWGCG Package (Devereux et al., (1984) Nucleic Acids Research 12, pp. 387-395), or PILEUP or BLAST algorisms (Altschul S. F. (1993) J Mol Evol 36: 290-300; Altschul S. F. (1990) J Mol Biol 215: 403-10).

Moreover, DOI synthases retaining high temperature stability can be selected from the DOI synthases obtained by the above-described methods by measuring the activities of the obtained enzymes after completion of a heat treatment.

[DOI Synthase Gene]

The DOI synthase gene of the present embodiment may be either a natural DOI synthase gene that is isolated and/or extracted from metagenome or microorganisms, or a DOI synthase gene synthesized based on its nucleotide sequence by a known method such as a PCR method or an artificial synthetic method. Furthermore, in order to produce a novel chimeric gene of DOI enzyme, a known DOI synthase gene may be used in combination. Examples of such a known DOI synthase gene include DOI synthase genes derived from a *Paenibacillus* sp. NBRC13157 strain, a *Streptoalloteichus hindustanus* JCM3268 strain, and a *Streptomyces fradiae* NBRC12773 strain, etc.

Specific examples of the nucleotide sequence of the DOI synthase gene according to the present embodiment are shown in SEQ ID NOS: 1, 3, 5, 7, 9 and 11.

A transformant is obtained from a recombinant vector comprising a DOI synthase gene having at least one gene sequence selected from the group consisting of the nucleotide sequences shown in SEQ ID NOS: 1, 3, 5, 7, 9 and 11, and a host. Thereafter, the obtained transformant is cultured, so as to obtain a DOI synthase.

A DOI synthase obtained from the DOI synthase gene having the nucleotide sequence shown in SEQ ID NO: 1, 3, 5, 7, 9 or 11 preferably has properties of high temperature stability and/or wide range pH stability.

In the present embodiment, the DOI synthase gene may have a nucleotide sequence having homology of preferably 80% or more, more preferably 85% or more, further preferably 90% or more, still further preferably 95% or more, and still further preferably 99% or more, with the DOI synthase gene having the nucleotide sequence shown in SEQ ID NO: 1, 3, 5, 7, 9 or 11. A DOI synthase gene, which has a nucleotide sequence having homology of 80% or more with at least one nucleotide sequence selected from the group consisting of the nucleotide sequences shown in SEQ ID NOS: 1, 3, 5, 7, 9 and 11, which has excellent properties of high temperature stability and/or wide range pH stability, and which encodes an enzyme having DOI synthase activity, is included in the present invention.

In the present embodiment, the DOI synthase gene may comprise a deletion, addition and/or substitution of one or multiple nucleotides with respect to the nucleotide sequence shown in any one of SEQ ID NOS: 1, 3, 5, 7, 9 and 11. A DOI synthase gene, which has a nucleotide sequence comprising a deletion, addition and/or substitution of one or multiple nucleotides with respect to the nucleotide sequence shown in any one of SEQ ID NOS: 1, 3, 5, 7, 9 and 11, and encoding a DOI synthase having high temperature stability and/or wide range pH stability, is included in the present invention. The number of nucleotides which are deleted, added and/or substituted is preferably 1 to 50, more preferably 1 to 30, further preferably 1 to 20, still further preferably 1 to 10, still further preferably 1 to 5, and still further preferably 1 to 3.

In the present embodiment, there may also be used a DOI synthase gene having a nucleotide sequence encoding the amino acid sequence described in any one of the following (a), (b) and (c):

(a) the amino acid sequence shown in any one of SEQ ID NOS: 2, 4, 6, 8, 10 and 12;

(b) an amino acid sequence having homology of 80% or more with the amino acid sequence shown in any one of SEQ ID NOS: 2, 4, 6, 8, 10 and 12, and having high temperature stability and/or wide range pH stability; and (c) an amino acid sequence comprising a deletion, addition and/or substitution of one or multiple amino acids with respect to the amino acid sequence shown in any one of SEQ ID NOS: 2, 4, 6, 8, 10 and 12, and having high temperature stability and/or wide range pH stability.

[Recombinant Vector and Transformant]

The recombinant vector of the present embodiment can be obtained by ligating (inserting) the gene of the present embodiment to (into) a known vector such as a plasmid. The type of such a known vector is not particularly limited, as long as it is able to replicate in a host. Examples of such a vector include plasmid DNA and phage DNA.

Examples of the aforementioned plasmid DNA include an *Escherichia coli*-derived plasmid (e.g. pBR322, pBR325, pUC18, pUC119, pTrcHis, pBlueBacHis, etc.), a *Bacillus subtilis*-derived plasmid (e.g. pUB110, pTPS, etc.), and a yeast-derived plasmid (e.g. YEp13, YEp24, YCp50, pYE52, etc.). An example of the aforementioned phage DNA is λ phage.

In order to insert the gene of the present embodiment into the aforementioned vector, there is applied a method comprising: first cleaving purified DNA by suitable restriction enzymes, and then inserting the thus cleaved DNA into the suitable restriction site or multicloning site of vector DNA, so as to ligate it to the vector.

In order to allow a foreign gene to express in a host, a suitable promoter needs to be located before a structural gene. The type of the promoter is not particularly limited, and any given promoter known to function in a host can be used. Such promoters will be described in detail for each type of host in the subsequent section regarding transformant. Moreover, if necessary, a cis-element such as an enhancer, a splicing signal, a poly(A) addition signal, a ribosome binding sequence (SD sequence), a terminator sequence and the like may be disposed.

The transformant of the present embodiment can be obtained by introducing the recombinant vector of the present embodiment into a host such that a gene of interest can be expressed therein. Herein, the type of the host is not particularly limited, as long as it is capable of expressing the DNA of the present embodiment. Examples of such a host include: bacteria belonging to genus *Escherichia* such as *Escherichia coli*, genus *Bacillus* such as *Bacillus subtilis*, genus *Pseudomonas* such as *Pseudomonas putida*, and genus *Rhizobium* such as *Rhizobium* meliloti; yeast such as *Saccharomyces cerevisiae*; animal cells such as COS cells and CHO cells; and insect cells such as Sf19 and Sf21.

In addition, a host used as the transformant of the present embodiment preferably has a function to synthesize glucose-6-phosphate from a monosaccharide such as glucose, fructose, galactose or xylose. Also, such a host preferably has a function to decompose a polysaccharide formed by ligation of two or more monosaccharides, as necessary.

From the viewpoint of efficient expression of a DOI synthase, when a bacterium such as *Escherichia coli* is used as a host, it is desired that the recombinant vector of the present embodiment can autonomously replicate in each bacterium, and also that the recombinant vector is constituted with a promoter, a ribosome-binding sequence, the gene of the present embodiment, and a transcription termination sequence. Moreover, a gene that controls the promoter may also be comprised in the vector. Examples of *Escherichia coli* include *E. coli* K12, DH1 and DH10B (Invitrogen), BL21-CodonPlus(DE3)-RIL (Stratagene), and TOP10F. Examples of *Bacillus subtilis* include *B. subtilis* MI114 and 207-21.

The type of a promoter is not particularly limited, as long as it functions in a host such as *Escherichia coli*. Examples of such a promoter used herein include: *Escherichia coli*-derived promoters such as a gapA promoter, a gadA promoter, a tip promoter, a lac promoter, a PL promoter or a PR promoter; and phage-derived promoters such as a T7 promoter.

The type of a method of introducing a recombinant vector into a bacterium is not particularly limited, as long as it enables introduction of DNA in the bacterium. Examples of such an introduction method include a method using a calcium ion (Cohen, S N et al., Proc. Natl. Acad. Sci. USA, 69: 2110 (1972)) and an electroporation method.

When a yeast is used as a host, *S. cerevisiae*, *Pichia pastoris* and the like are used, for example. In this case, as a promoter, a promoter capable of being expressed in such a yeast can be used Examples of such a promoter include a gall promoter, a gal10 promoter, a heat shock protein promoter, an MFα1 promoter, a PHOS promoter, and an AOX promoter.

Examples of a method of introducing a recombinant vector into a yeast include an electroporation method (Becker, D. M. et al.: Methods. Enzymol., 194: 180 (1990)), a spheroplast method (Hinnen, A. et al.: Proc Natl. Acad. Sci. USA, 75: 1929 (1978)), and a lithium acetate method (Itch, H.: J. Bacteriol., 153: 163 (1983)).

[Production of DOI Synthase]

The enzyme of the present embodiment can be obtained by culturing the transformant of the present embodiment in a suitable medium, and then collecting a protein having the activity of the enzyme from the culture. A method of culturing the transformant of the present embodiment may be determined depending on the type of a host. For example, in the case of a transformant whose host is a microorganism such as *Escherichia coli* or a yeast, either a natural medium or a synthetic medium may be used, as long as it contains a carbon source, a nitrogen source, inorganic salts and the like, which can be assimilated by the microorganism, and is able to efficiently culture the transformant.

During the culture, an antibiotic such as ampicillin or tetracycline may be added to the medium, as necessary. In the case of culturing a microorganism that has been transformed with an expression vector comprising an inducible promoter, an inducer may be added to the medium, as necessary. For example, in the case of culturing a microorganism that has been transformed with an expression vector comprising a lac promoter, isopropyl-β-thiogalactopyranoside (IPTG) or the like may be added to the medium, and in the case of culturing a microorganism that has been transformed with an expression vector comprising a tip promoter, indole acrylic acid (IAA) or the like may be added to the medium.

After completion of the culture, if the enzyme protein of the present embodiment is produced inside the cell mass or cells, the cells are disintegrated. On the other hand, the protein of the present embodiment is secreted outside the cell mass or cells, the culture solution is used as is, or the protein is recovered by centrifugation or the like.

For isolation and/or purification of the protein, for example, ammonium sulfate precipitation, gel filtration, ion exchange chromatography, affinity chromatography and the like may be used singly or in combination, as appropriate.

The term "activity" is used herein to mean the activity of converting glucose-6-phsophate to DOI. A method of measuring an activity value is as described below.

The activity of the DOI synthase of the present embodiment can be confirmed by a method comprising adding the enzyme to a reaction solution containing suitable glucose-6-phosphate serving as a substrate and then detecting the generated DOI. The generated DOI can be confirmed by applying the method described in a Non-Patent Document (Journal of Biotechnology 129, 502-509 (2007)).

As a method of measuring the DOI synthase activity, there is applied a method comprising: mixing 100 μL of a DOI synthase solution having an appropriate concentration into 900 μL, of a 150 mM Bis-Tris buffer (pH 7.0) containing 20 μL of 1000 mM glucose-6-phosphate solution, 50 μL of 100 mM NAD$^+$ solution and 50 μL of 100 mM cobalt chloride hexahydrate solution; reacting the obtained mixture for approximately 5 to 60 minutes; deactivating the enzyme; and then quantifying DOI.

Confirmation of the purification degree of the purified DOI synthase and the measurement of a molecular weight can be carried out by electrophoresis, gel filtration chromatography, etc. In addition, the optimum temperature range or optimum pH range of the enzyme may be obtained by measuring the enzyme activity, while changing the reaction temperature or the reaction pH. Moreover, the stable pH range or stable temperature range of the enzyme may also be obtained by exposing the DOI synthase to various pH conditions or temperature conditions for a certain period of time, and then measuring the enzyme activity. Bis-Tris buffer (pH 5.5 to 8.0) and Tris buffer (pH 7.4 to 8.0) may be used to evaluate the DOI synthase under various pH conditions.

The term "optimum pH range" is used herein to mean a pH range in which the activity value is 70 or greater, when the highest activity value obtained by measuring the activity value of the enzyme while changing pH is set at 100.

The term "stable pH range" is used herein to mean a pH range in which the activity value is 70 or greater, when the highest activity value obtained by measuring the activity value of the enzyme while changing pH is set at 100.

The term "optimum temperature range" is used herein to mean a temperature range in which the activity value is 50 or greater, when the highest activity value obtained by measuring the activity value of the enzyme while changing pH is set at 100.

The term "stable temperature range" is used herein to mean a temperature range in which the activity value is 50 or greater, when the highest activity value obtained by measuring the activity value of the enzyme while changing pH is set at 100.

The term "high temperature stability" in the high temperature stability of the DOI synthase of the present embodiment is used herein to mean that the upper limit of the stable temperature range is 46° C., more preferably 50° C., further preferably 60° C., still further preferably 70° C., still further preferably 80° C., still further preferably 90° C., and particularly preferably 95° C. The lower limit of the stable temperature range is not particularly limited. Taking into consideration ordinary operations, the lower limit of the stable temperature range may be, for example, 20° C., preferably 10° C., more preferably 5° C., and further preferably 1° C.

As the 2-deoxy-scyllo-inosose synthase of the present embodiment having high temperature stability, an enzyme having a residual enzyme activity of 50 or greater after incubation at 50° C. for 1 hour can be selected, for example. The term "residual enzyme activity" is used herein to indicate relative activity obtained when the highest activity value is set at 100.

In general, in an industrial enzyme reaction, the temperature needs to be controlled within a temperature range in which the enzyme has high activity, and thus, the control of the temperature becomes an extremely important factor.

From the viewpoint of the activity of bacteria, in the synthesis of DOI, a strict temperature control, in which the temperature is controlled at 37° C. or lower, has conventionally been required. If a DOI synthase having high temperature stability is used, it becomes possible for the enzyme to maintain high activity even in a high temperature range. As a result, it becomes possible to produce DOI without such strict temperature control.

The DOI synthase according to the present embodiment having wide range pH stability has characteristics, in which the stable pH range is preferably pH 6.0 to 7.0, more preferably pH 6.0 to 7.4, further preferably pH 6.0 to 7.7, still further preferably pH 6.0 to 8.0, and particularly preferably pH 4.0 to 9.0.

From the viewpoint of maintaining the high activity of bacteria, in the conventional DOI synthesis, a strict pH control, in which the pH value is controlled at pH 6.0 to 7.0, has conventionally been required. If a DOI synthase having wide range pH stability is used, it becomes possible for the enzyme to maintain high activity even in a wide pH range. As a result, it becomes possible to produce DOI without such strict pH control.

The enzyme of the present embodiment is not required to have high purity, unless its action is inhibited. Hence, purification is not essential, and the enzyme of the present embodiment may comprise other enzymes and the like.

[Production of DOI]

The DOI of the present embodiment can be obtained by a fermentative production method comprising culturing the transformant of the present embodiment and then collecting DOI from the culture.

As a nutrient source for the above-described culture, there can be used a medium that contains a carbon source, a nitrogen source, inorganic salts and other organic nutrient sources. The culture temperature is not particularly limited, as long as it is a temperature at which the bacteria can grow. The culture time is not particularly limited, and it may be approximately 1 to 7 days. Thereafter, DOI may be recovered from the obtained culture cell mass or culture supernatant.

A polysaccharide comprising glucose as a constituent may be directly used as a carbon source in the culture, as long as it can be assimilated by the transformant. More preferred examples of such a carbon source include a monosaccharide, and a monosaccharide derived from a raw material containing a polysaccharide such as starch, rice bran or blackstrap molasses. A specific example is D-glucose. When the expression of a promoter is an inducible type, an inducer may be added on a timely basis.

Examples of a carbon source that can be used herein include: sugars such as D-glucose, galactose, maltose, saccharose or treharose; oils and fats; fatty acids; and n-paraffin Examples of such oils and fats include rapeseed oil, coconut oil, palm oil and palm kernel oil. Examples of such fatty acids include: saturated or unsaturated fatty acids such as hexanoic acid, octanoic acid, decanoic acid, lauric acid, oleic acid, palmitic acid, linoleic acid, linolenic acid or myristic acid; and fatty acid derivatives such as fatty acid esters or salts.

Examples of an organic nutrient source include amino acids such as adenine, histidine, leucine, uracil or tryptophan.

Examples of a nitrogen source include: ammonia; ammonium salts such as ammonium chloride, ammonium sulfate or ammonium phosphate; peptone; meat extract; and yeast extract. Examples of inorganic salts include sodium hydrogen phosphate, potassium dihydrogen phosphate, magnesium chloride, magnesium sulfate and sodium chloride.

In the present invention, DOI can be produced from glucose-6-phosphate by culturing microorganisms capable of expressing a DOI synthase in a medium containing a cobalt ion.

In the method for producing DOI according to the present embodiment, the cobalt ion is preferably used in the form of the salt of a divalent cobalt ion. Specific examples include cobalt chloride, cobalt sulfate and cobalt acetate.

When a cobalt ion is added to a culture solution, the productivity of DOI is improved, when compared with a culture in which no cobalt ions are added. If such cobalt ions are excessively added to the culture solution, it may cause growth inhibition of microorganisms. Accordingly, the cobalt concentration during the culture may be set within a range that is sufficient for the enzyme to possess activity and does not inhibit the growth of microorganisms. The appropriate cobalt concentration depends on the type of a host. When *Escherichia coli* is used as a host, for example, it is preferable that the cobalt concentration immediately after initiation of the culture be maintained at a concentration of preferably 0.1 to 200 mg/L, more preferably 0.1 to 100 mg/L, and further preferably 0.1 to 50 mg/L, relative to cobalt chloride hexahydrate. The expression "immediately after initiation of the culture" is used herein to mean a range from initiation of the main culture to the time point at which the cell solution OD reaches 5. The "cell solution OD" means the optical density of a culture solution, and in the present embodiment, it indicates the absorption intensity of a culture solution with respect to light at 600 nm.

When a high-density culture is applied, with an increase in the concentration of a cell mass in the culture solution, carbon sources such as glucose, which are raw materials of constituents in a microorganism cell mass, such as proteins, nucleic acids, lipids or vitamins, and which serve as energy sources necessary for the growth of the microorganisms, become insufficient. In such a case, carbon sources are continuously or intermittently supplied to the culture solution. In the present embodiment, cobalt ions are further added to the culture solution, so that cobalt ions necessary for the expression of the activity of the enzyme can preferably be supplied in appropriate amounts, continuously or intermittently.

In the method for producing DOI of the present embodiment, the added cobalt value is controlled to be preferably 0.0003 to 70, more preferably 0.001 to 15, and further preferably 0.01 to 5. The added cobalt value was calculated by the following formula:

Added cobalt value=[the total amount of cobalt chloride hexahydrate (mg) added to the culture solution]/the amount of the culture solution (L)/cell solution *OD*

When cobalt salts other than cobalt chloride hexahydrate is used, the added cobalt value may be calculated relative to cobalt chloride hexahydrate, and cobalt salts may be then added, so that the amount of cobalt ions becomes an appropriate value.

As a method of recovering DOI from a culture solution, the following method is applied.

After completion of the culture, a cell mass is removed from the culture using a centrifuge or a filter, so as to obtain a culture supernatant. This culture supernatant is further subjected to a filtration treatment, so as to remove solids such as a cell mass. Then, an ion exchange resin is added to the filtrate, and elution is then carried out with distilled water. The resultant is measured in terms of ICP emission analysis, pH and the like, and at the same time, a fraction containing no impurities is separated. Solvents are removed from the aqueous solution thereof, so as to recover DOI.

The obtained DOI is analyzed, for example, by high performance liquid chromatography, nuclear magnetic resonance, etc.

Other than the above-described fermentative production method, there is applied a method using glucose-6-phosphate converted from glucose by the action of glucokinase or the like. Using the DOI synthase of the present embodiment or a transformant, DOI can be obtained from glucose-6-phosphate.

In view of the reaction rate or the stability of the enzyme, the reaction temperature applied during the production of DOI using the DOI synthase of the present embodiment and/ or a transformant is preferably 10° C. to 95° C., more preferably 20° C. to 70° C., and further preferably 30° C. to 60° C.

The reaction pH can be adjusted in a broad range. In view of the stability of the enzyme, the reaction pH is preferably pH 2.0 to 10.0, more preferably pH 4.0 to 8.0, and further preferably 6.0 to 8.0.

The reaction time depends on the amount of the enzyme used. Taking into consideration industrial use thereof, the reaction time is generally 20 minutes to 200 hours, and more preferably 6 to 80 hours. When a transformant is used as a DOI synthetic catalyst, it may previously be subjected to a freezing treatment or various types of crushing treatments.

However, the present embodiment is not limited to the above-described reaction conditions or reaction embodiments, and it may be selected, as appropriate.

Hereinafter, the present invention will be more specifically described in the following examples. These examples are not intended to limit the scope of the present invention.

EXAMPLES

Example 1

(1) Preparation of Chromosomal DNA

The chromosomal DNA of a *Paenibacillus* sp. NBRC13157 strain was prepared according to an ordinary method.

The *Paenibacillus* sp. NBRC13157 strain was cultured at 30° C. for 1 day on an NR agar plate (1% Bacto Tryptone, 0.2% Yeast Extract, 1% Ehrlich's bonito extract, and 1.5% Bacto Agar; pH7.0), so as to form a colony. Thereafter, a platinum loop of the colony was inoculated into 30 mL of an NR medium (1% Bacto Tryptone, 0.2% Yeast Extract, and 1% Ehrlich's bonito extract; pH7.0) that had been dispensed into a 150-mL Erlenmeyer flask. The obtained mixture was cultured at 30° C. at 180 rpm for 1 day. Thereafter, the obtained culture solution was centrifuged at 4° C. at 12,000 g for 1 minute, the supernatant was then removed, and the cell mass was then recovered.

The obtained cell mass was suspended in a lysis buffer (50 mM Tris-HCl (pH 8.0), 20 mM EDTA, and 50 mM glucose), and was fully washed. The cell mass was recovered by centrifugation, and it was then re-suspended in a lysis buffer. To the suspension, lysozyme was added, and the obtained mixture was then incubated at 37° C. for 45 minutes. Subsequently, SDS and RNase were added to the reaction solution, and the obtained mixture was then incubated at 37° C. for 45 minutes. Thereafter, Proteinase K was added to the reaction solution, and the obtained mixture was then gently shaken at 50° C. for 60 minutes. The obtained solution was treated with phenol-chloroform and chloroform, and was then subjected to ethanol precipitation. The precipitated nucleic acid was recovered by winding it around a glass pipette. This nucleic acid was washed with 70% ethanol, was dried, and was then re-suspended in TE. By this operation, approximately 100 µg of chromosomal DNA was prepared.

(2) Isolation of DOI Synthase Gene

PCR primers for amplification of a DOI synthase gene from the chromosomal DNA prepared in (1) above, were synthesized. That is, oligo DNA having the sequence shown in SEQ ID NO: 15 was synthesized as a sense primer, and oligo DNA having the sequence shown in SEQ ID NO: 16 was synthesized as an antisense primer.

Using the thus obtained PCR primers, and also using the chromosomal DNA prepared in (1) above as a template, a DOI synthase gene was amplified according to a PCR method, and as a result, a PCR product consisting of 1107 base pairs was obtained.

The gene sequence of the obtained PCR product was confirmed by analyzing it with a DNA sequencer, so as to obtain a known DOI synthase (BtrC) gene having the nucleotide sequence shown in SEQ ID NO: 13. The amino acid sequence corresponding to this gene was shown in SEQ ID NO: 14 (BtrC).

(3) Construction of Expression Plasmid Vector of DOI Synthase Gene and Transformation A blunt end treatment and phosphorylation were performed on the PCR product obtained in (2) above, and the resultant product was then ligated to a plasmid formed by linking an *Escherichia coli*-derived gapA promoter, an SD sequence and a terminator to pUC19. Into this plasmid vector, a gapA promoter capable of efficiently transcribing a gene ligated as a foreign gene in *Escherichia coli* had been introduced. Thus, even in a case in which recombinant microorganisms are cultured in a medium containing glucose, the DOI synthase can be efficiently expressed and produced.

The competent cells of *Escherichia coli* JM109 strain prepared by a calcium chloride method were transformed with the thus obtained plasmid vector according to a heat shock method, so as to prepare recombinant microorganisms.

(4) Obtainment of Novel DOI Synthase Gene

Mutations were introduced into the plasmid vector obtained in (3) above according to an ordinary method, so as to obtain heat-resistant DOI synthase genes having the nucleotide sequences shown in SEQ ID NO: 1 (DOIS-1), SEQ ID NO: 3 (DOIS-2), SEQ ID NO: 5 (DOIS-3), SEQ ID NO: 7 (DOIS-4), SEQ ID NO: 9 (DOIS-5) and SEQ ID NO: 11 (DOIS-6). Also using the thus obtained DOI synthase genes, transformants were obtained in the same manner as that of (3) above. Moreover, amino acid sequences corresponding to the nucleotide sequences of SEQ ID NO: 1, SEQ ID NO: 3, SEQ ID NO: 5, SEQ ID NO: 7, SEQ ID NO: 9 and SEQ ID NO: 11 are shown in SEQ ID NO: 2 (DOIS-1), SEQ ID NO: 4 (DOIS-2), SEQ ID NO: 6 (DOIS-3), SEQ ID NO: 8 (DOIS-4), SEQ ID NO: 10 (DOIS-5) and SEQ ID NO: 12 (DOIS-6).

The novel DOI synthase can be selected by subjecting various DOI synthases produced by ordinary methods to a heat treatment or various pH treatments, and then measuring the activity thereof.

Example 2

Obtainment of Purified Enzyme

The transformant of DOI synthase (DOIS-1) produced in Example 1 was cultured at 37° C. for 1 day on an LB plate containing 100 mg/L ampicillin, so as to form a colony.

Subsequently, 30 mL of an LB medium containing 100 mg/L ampicillin was placed in a 150-mL Erlenmeyer flask, and the colony formed in the above-described plate was inoculated into the medium using a platinum loop. The obtained mixture was subjected to a rotary shaking culture at 37° C. at 180 rpm for 3 to 8 hours, until OD (600 nm) became approximately 0.5. The obtained reaction solution was used as a pre-culture solution in the main culture.

100 ml of an LB medium containing 2 g/L glucose and 100 mg/L ampicillin was placed into each of thirty-six 500-mL Erlenmeyer flask, and 0.5 mL of the pre-culture solution was then added to each of the Erlenmeyer flasks. The obtained mixture was subjected to a rotary shaking culture at 37° C. at 180 rpm for 16 hours.

Subsequently, the culture solution was centrifuged at 4° C. at 10,000 g×30 minutes to remove the supernatant, and the cell mass was then recovered while washing the residue with a 50 mM Tris-HCl buffer (pH 7.7) containing 0.2 mg/L cobalt chloride hexahydrate several times. The recovered cell mass was cryopreserved at −80° C.

This cryopreserved cell mass was suspended in a 50 mM Tris-HCl buffer (pH 7.7) containing 0.2 mg/L cobalt chloride hexahydrate, and 180 mg of lysozyme (derived from albumen; manufactured by Sigma) and 60 μL of deoxyribonucleoase I (bovine-derived recombinant solution, manufactured by WaKo) were then added to the suspension. The obtained mixture was stirred at 37° C. at 120 rpm for 5 hours to disintegrate the cell mass.

After completion of the cell mass disintegration, the resultant solution was centrifuged at 4° C. at 10,000 g×30 minutes to remove the cell mass residue, so as to recover a supernatant.

This supernatant was brought to 30% saturation by addition of ammonium sulfate, and it was then stirred at 4° C. for a while. Thereafter, the generated precipitate was removed by centrifugation at 4° C. at 10,000 g×30 minutes, so as to recover a supernatant.

This supernatant was brought to 40.0% saturation by further addition of ammonium sulfate, and it was then stirred at 4° C. for a while. Thereafter, the generated precipitate was centrifuged at 4° C. at 10,000 g×30 minutes to remove a supernatant, so as to recover a precipitate. Subsequently, this precipitate was dissolved in 50 mM Tris-HCl buffer (pH 7.7) containing 0.2 mg/L cobalt chloride hexahydrate.

The dissolved solution was concentrated at 4° C. using an ultrafiltration membrane having a mean fractional molecular weight of 10,000, and 50 mM Tris-HCl buffer (pH 7.7) containing 0.2 mg/L cobalt chloride hexahydrate was then added to the concentrate, followed by concentration again. This desalting operation was repeatedly carried out two or three times.

The thus obtained enzyme solution was adsorbed on "DEAE Sepharose FF" (GE Healthcare Biosciences) that had been equilibrated with 50 mM Tris-HCl buffer (pH 7.7), and the enzyme was then eluted by a concentration gradient method using 50 mM Tris-HCl buffer (pH 7.7) containing 0 to 0.4 M sodium chloride.

The active fractions of DOI synthases as eluted above were collected, and the collected fraction was then concentrated using an ultrafiltration membrane having a mean fractional molecular weight of 10,000. The concentrate was suspended in 50 mM Tris-HCl buffer (pH 7.7) containing 10% by weight of ammonium sulfate. The thus obtained solution was adsorbed on "HiTrap Phenyl FF (high sub)" (GE Healthcare Biosciences) that had been equilibrated with 50 mM Tris-HCl buffer (pH 7.7) containing 10% by weight of ammonium sulfate, and the enzyme was then eluted by a concentration gradient method using 50 mM Tris-HCl buffer (pH 7.7) containing 10% to 0% by weight of ammonium sulfate.

The thus eluted active fractions were collected, and the collected fraction was then concentrated using an ultrafiltration membrane having a mean fractional molecular weight of 10,000. The concentrate was adsorbed on "Mono Q 5/50 GL" (GE Healthcare Biosciences) that had been equilibrated with 50 mM Tris-HCl buffer (pH 7.7), and the enzyme was then eluted by a concentration gradient method using 50 mM Tris-HCl buffer (pH 7.7) containing 0 to 0.2 M sodium chloride.

The thus eluted active fractions were collected, and the collected fraction was then concentrated using an ultrafiltration membrane having a mean fractional molecular weight of 10,000. The concentrate was filled into "HiLoad 16/60 Superdex 200" (GE Healthcare Biosciences) that had been equilibrated with a 50 mM Tris-HCl buffer (pH 7.7) containing 0.2 mg/L cobalt chloride hexahydrate and 0.1 M NaCl, and the enzyme was then eluted using the same buffer as described above.

The thus eluted active fractions were collected, and the collected fraction was then concentrated using an ultrafiltration membrane having a mean fractional molecular weight of 10,000, so as to obtain a purified DOI synthase (DOIS-1).

A purified DOI synthase (DOIS-2), a purified DOI synthase (DOIS-3), a purified DOI synthase (DOIS-4), a purified DOI synthase (DOIS-5), a purified DOI synthase (DOIS-6) and a known DOI synthase (BtrC) were obtained in the same manner as that in the above-described series of experiments for obtaining a purified enzyme.

Example 3

Evaluation of Novel DOI Synthases

Using the purified DOI synthases obtained in Example 2, an experiment was carried out to examine their actions.
(1) Optimum pH Range
In the measurement of the enzyme activity at various pH values, an appropriate amount of the purified DOI synthase (DOIS-1) was added to the reaction solution, and the reaction solution was then adjusted so that it comprised 20 mM glucose-6-phosphate disodium salt (Oriental Yeast Co., Ltd.), 5 mM NAD+ (Oriental Yeast Co., Ltd.), 5 mM cobalt chloride hexahydrate and 100 mM of various types of buffers. As buffers, Bis-Tris buffer (pH 6.0 to 7.7) and Tris buffer (pH 7.4 to 8.0) were used. The reaction temperature was set at 30° C., and the activity was measured by quantifying the generated DOI. Relative activity was obtained while setting the highest activity value at 100. The results are shown in FIG. 1. The optimum pH range for the enzyme of the present invention was found to be pH 7.0 to 7.7.
(2) Stable pH Range
Using 100 mM buffers having its pH value in the range from pH 5.5 to 8.0, the purified DOI synthase (DOIS-1) was incubated at each pH value at 30° C. for 60 minutes. Thereafter, the residual enzyme activity was measured. Bis-Tris buffer (pH 5.5 to 8.0) and Tris buffer (pH 7.4 to 8.0) were used in the incubation.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 2. The stable pH range for the present enzyme was found to be pH 6.0 to 8.0. The purified DOI synthase (DOIS-2) and the purified DOI synthase (DOIS-3) had the same results as those for DOIS-1. Such wide range pH stability was a novel property, which had not been possessed by the existing enzymes.
(3) Optimum Temperature Range
The enzyme activity of the purified DOI synthase (DOIS-1) was measured under various reaction temperature conditions (a reaction temperature range from 10° C. to 70° C.) in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 3. The optimum temperature range for the present enzyme was found to be 55° C. to 70° C. The specific activity at a reaction temperature of 65° C. was extremely high (1.8 μmol (DOT)/min/mg (enzyme)).
(4) Stable Temperature Range
100 mM Bis-Tris buffer (pH 7.0), to which the purified DOI synthase (DOIS-1) had been added and which had been adjusted to comprise 5 mM NAD+ (Oriental Yeast Co., Ltd.) and 5 mM cobalt chloride hexahydrate, was incubated at various temperatures in a temperature range from 25° C. to 60° C. for 1 hour. Thereafter, the residual enzyme activity in each case was measured.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 4. The stable temperature range for the purified DOI synthase (DOIS-1) was found to be 50° C. or lower. The purified DOI synthase (DOIS-2) and the purified DOI synthase (DOIS-3) had the same results as those for DOIS-1. Such high temperature stability was a novel property, which had not been possessed by the existing enzymes.

Moreover, an experiment regarding stable temperature range was carried out by incubating the enzyme in the absence of NAD+ and cobalt ions known to be act as stabilizers. As a result, the relative activity of the purified DOI synthase (DOIS-1) was 38 at an incubation temperature of 46° C. The relative activity thereof was 89 at an incubation temperature of 42° C. and was 100 at an incubation temperature of 37° C.
(5) Molecular Weight
The molecular weight of the enzyme was measured by SDS-polyacrylamide gel electrophoresis using "Ready-Gel J" (Bio-Rad Laboratories, Inc.) having a separated gel concentration of 10%. As a result, the molecular weight of the purified DOI synthase (DOIS-1) was found to be approximately 40,000. This molecular weight was almost the same as the putative molecular weight (40,656) assumed from its amino acid sequence.

Example 4

Evaluation of Novel DOI Synthases

Using the purified DOI synthase (DOTS-4) obtained in Example 2, an experiment was carried out to examine its action.
(Evaluation of Temperature Stability)
100 mM Bis-Tris buffer (pH 7.0), to which the purified DOI synthase (DOIS-4) had been added and which had been adjusted to comprise 5 mM cobalt chloride hexahydrate, was incubated at each temperature of 25° C. and 42° C. for 1 hour. Thereafter, the residual enzyme activity in each case was measured.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. When the residual activity obtained after incubation at 25° C. was set at 100, the activity value obtained after incubation at 42° C. became extremely high (74).
(Measurement of Specific Activity)
The specific activity at a reaction temperature of 60° C. became an extremely high value (1.2 μmol (DOT)/min/mg (enzyme)).

Example 5

Evaluation of Novel DOI Synthases

Using the purified DOI synthase (DOIS-5) obtained in Example 2, an experiment was carried out to examine its action.

(Evaluation of pH Stability)

Using 100 mM buffers each having a pH value in a pH range from pH 5.5 to 8.0, the purified DOI synthase (DOIS-5) was incubated at each pH value at 30° C. for 60 minutes, and thereafter, the residual enzyme activity was measured. Bis-Tris buffer (pH 5.5 to 8.0) and Tris buffer (pH 7.4 to 8.0) were used in the incubation.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 5. As shown in FIG. 5, the present enzyme showed high stability in an extremely wide pH range. This high stability was a novel property, which had not been possessed by the existing enzymes.

Example 6

Evaluation of Novel DOI Synthases

Using the purified DOI synthase (DOIS-6) obtained in Example 2, an experiment was carried out to examine its action.
(Evaluation of pH Stability)

Using 100 mM buffers each having a pH value in a pH range from pH 5.5 to 8.0, the purified DOI synthase (DOIS-6) was incubated at each pH value at 30° C. for 60 minutes, and thereafter, the residual enzyme activity was measured. Bis-Tris buffer (pH 5.5 to 8.0) was used in the incubation.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. When the residual activity at pH 8.0 at which the highest activity had been obtained was set at 100, the activity value was 70 or greater in a pH range from pH 6.5 to 8.0, and the residual activity at pH 6.0 was an extremely high value (53). This high pH stability was a novel property, which had not been possessed by the existing enzymes.

Example 7

Method for Producing DOI

The transformant of DOI synthase (DOIS-1) produced in Example 1 was cultured at 37° C. for 1 day on an LB plate containing 100 mg/L ampicillin, so as to form a colony.

Subsequently, 30 mL of an LB medium containing 100 mg/L ampicillin was placed in a 150-mL Erlenmeyer flask, and the colony formed in the above-described plate was inoculated into the medium using a platinum loop. The obtained mixture was subjected to a rotary shaking culture at 37° C. at 180 rpm for 3 to 8 hours, until OD (600 nm) became approximately 0.5. The obtained reaction solution was used as a pre-culture solution in the main culture.

100 ml of an LB medium containing 2 g/L glucose and 100 mg/L ampicillin was placed into each of thirty-six 500-mL Erlenmeyer flask, and 0.5 mL of the pre-culture solution was then added to each of the Erlenmeyer flasks. The obtained mixture was subjected to a rotary shaking culture at 37° C. at 180 rpm for 16 hours.

Subsequently, the culture solution was centrifuged at 4° C. at 10,000 g×30 minutes to remove the supernatant, and the cell mass was then recovered while washing the residue with 50 mM Tris-HCl buffer (pH 7.7) containing 0.2 mg/L cobalt chloride hexahydrate several times. The recovered cell mass was cryopreserved at −80° C.

In the synthesis of DOI, a solution prepared by suspending the above-described cell mass in 50 mM Tris-HCl buffer (pH 7.7) containing 0.2 mg/L cobalt chloride hexahydrate was used as a DOI synthetic catalyst. The composition of a reaction solution used in the DOI synthetic reaction was 85 mM glucose-6-phosphate disodium salt (Oriental Yeast Co., Ltd.), 0.1 mM NAD+ (Oriental Yeast Co., Ltd.) and 1 mM cobalt chloride hexahydrate, wherein cell mass OD was 30. Using this reaction solution, the DOI synthetic reaction was initiated. The pH at the initiation of the reaction was adjusted to be pH 7.7, and the synthetic reaction was carried out at a reaction temperature of 46° C. for 2.5 hours. As a result, 1% by weight of DOI was generated. After completion of the reaction, hydrochloric acid was added to the reaction solution, so that the pH was decreased to pH 6 or less. Subsequently, this reaction solution was centrifuged at 4° C. at 10,000 g×30 minutes to recover a supernatant. It was then filtrated with a filter to remove a cell mass residue.

The synthesized DOI solution was subjected to a purification treatment using a cation exchange resin, in which Amberlite IR120 BNa (manufactured by Organo Corp.) was reproduced to H+ type, and an anion exchange resin, in which Amberlite IRA96SB (manufactured by Organo Corp.) was reproduced to OFF type. In this purification treatment, a column treatment was used in combination with a batch treatment, and a fraction, in which P, Co and Na had not been detected and comprised a DOI solution, was recovered by an ICP emission analysis method.

Subsequently, to the obtained DOI solution, activated carbon Carborafin (manufactured by Japan EnviroChemicals, Ltd.) was added in an amount of 0.5 g with respect to 1 g of DOI contained in the DOI solution. The obtained mixture was stirred at room temperature for 1 hour, so that a trace amount of impurity was adsorbed on the activated carbon. One hour later, the activated carbon was removed by a filtration operation, and the DOI solution was then recovered. DOI was concentrated by subjecting the recovered DOI solution to vacuum concentration, and the concentrate was then freeze-dried to obtain DOI powders.

Example 8

The transformant of DOI synthase (DOIS-1) produced in Example 1 was cultured at 37° C. for 1 day on an LB plate containing 100 mg/L ampicillin, so as to form a colony.

Subsequently, 30 mL of an LB medium containing 100 mg/L ampicillin was placed in a 150-mL Erlenmeyer flask, and the colony formed in the above-described plate was inoculated into the medium using a platinum loop. The obtained mixture was subjected to a rotary shaking culture at 37° C. at 180 rpm for 3 to 8 hours, until OD became approximately 0.5. The reaction solution was used as a pre-culture solution in the main culture.

100 mL of medium A containing the cobalt chloride hexahydrate each having a different concentration shown in Table 1 below was placed in a 500-mL Erlenmeyer flask, and 0.5 mL of the pre-culture solution was then added thereto. The obtained mixture was subjected to a rotary shaking culture at 37° C. at 180 rpm for 18 hours. Eighteen hours after initiation of the culture, the cell solution OD under various medium conditions, added cobalt value, and relative value (DOI productivity) obtained when the DOI concentration in the supernatant of a cobalt ion-non-added medium was set at 100, are shown in Table 2 below

TABLE 1

| Medium A | |
| --- | --- |
| Potassium dihydrogen phosphate | 2 g/L |
| Diammonium hydrogen phosphate | 3 g/L |
| Magnesium sulfate heptahydrate | 0.2 mg/L |
| Thiamine hydrochloride | 20 mg/L |
| Yeast extract | 3 g/L |
| Glucose | 10 g/L |
| Cobalt chloride hexahydrate | 0 to 20 mg/L |

(*) The above substances were dissolved in distilled water, and the pH value was then adjusted to pH 7.0.

TABLE 2

| Added concentration of cobalt chloride hexahydrate (mg/L) | Cell solution OD | Added cobalt value | Relative value (DOI productivity) |
| --- | --- | --- | --- |
| 0 | 4.2 | 0.00 | 100 |
| 0.1 | 4.3 | 0.02 | 114 |
| 0.5 | 4.4 | 0.11 | 118 |
| 1 | 4.3 | 0.23 | 124 |
| 3 | 4.2 | 0.71 | 131 |
| 5 | 4.3 | 1.17 | 125 |
| 7 | 4.0 | 1.77 | 114 |
| 10 | 4.3 | 2.30 | 122 |
| 20 | 4.6 | 4.37 | 122 |

Comparative Example 1

Evaluation of Known DOI Synthase

The known purified DOI synthase (BrtC) having the amino acid sequence shown in SEQ ID NO: 14 was subjected to the following experiments in the same manner as that of Example 3-(4) "Stable temperature range."

100 mM Bis-Tris buffer (pH 7.0), to which the purified DOI synthase (BtrC) had been added and which had been adjusted to comprise 5 mM NAD+ (Oriental Yeast Co., Ltd.) and 5 mM cobalt chloride hexahydrate, was incubated at various temperatures in a temperature range from 25° C. to 60° C. for 1 hour. Thereafter, the residual enzyme activity in each case was measured.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 6. The stable temperature range of the purified known DOI synthase (BtrC) was found to be 42° C. or lower. The relative activity at 46° C. was 23, and the relative activity at 50° C. was 0. Thus, the purified known DOI synthase (BtrC) showed significantly low heat stability.

Moreover, an experiment regarding stable temperature range was carried out by incubating the enzyme in the absence of NAD+ and cobalt ions known to be act as stabilizers. As a result, the relative activity of the purified known DOI synthase (BtrC) was 0 at incubation temperatures of 42° C. and 46° C., and the relative activity thereof at 37° C. was 14. Also from this experiment, it was found that the existing enzyme has significantly low heat stability.

The purified known DOI synthase (BrtC) having the amino acid sequence shown in SEQ ID NO: 14 was subjected to the following experiments in the same manner as that of Example 3-(2) "Stable pH range."

The purified known DOI synthase (BrtC) was incubated at each pH value at 30° C. for 60 minutes, and the residual enzyme activity was then measured. Bis-Tris buffer (pH 5.5 to 8.0) and Tris buffer (pH 7.4 to 8.0) were used in the incubation.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. Relative activity was obtained while setting the highest activity value at 100. The results are shown in FIG. 7. As shown in FIG. 7, the relative activity at pH 6 was extremely low (27), and the present enzyme was almost completely deactivated at pH 5.5.

Comparative Example 2

Evaluation of Known DOI Synthase

The purified known DOI synthase (BrtC) having the amino acid sequence shown in SEQ ID NO: 14 was subjected to the following experiments in the same manner as that of Example 3.

100 mM Bis-Tris buffer (pH 7.0), to which the purified known DOI synthase (BtrC) had been added and which had been adjusted to comprise 5 mM cobalt chloride hexahydrate, was incubated at temperatures of 25° C. and 42° C. for 1 hour. Thereafter, the residual enzyme activity in each case was measured.

The residual enzyme activity was measured at a reaction temperature of 30° C. in 100 mM Bis-Tris buffer (pH 7.0) which comprised 20 mM glucose-6-phosphate disodium salt (Oriental Yeast Co., Ltd.), 5 mM NAD+ (Oriental Yeast Co., Ltd.) and 5 mM cobalt chloride hexahydrate. When the residual activity obtained after completion of the incubation at 25° C. was set at 100, the activity value after completion of the incubation of 42° C. became 0. Thus, the purified known DOI synthase (BtrC) showed significantly low heat stability.

INDUSTRIAL APPLICABILITY

According to the present invention, it becomes possible to produce DOI that is extremely useful as a precursor of industrially useful aromatic compounds (catechol, etc.) by an efficient production process.

The invention claimed is:

1. An isolated 2-deoxy-scyllo-inosose synthase having any one of the following amino acid sequences:
   (a) amino acid sequences of SEQ ID NO: 2, 4, 6, and 8; and
   (b) an amino acid sequence having sequence identity of 95% or more with the amino acid sequence of SEQ ID NO: 2, and having temperature stability between 20° C. and 50° C. and/or pH stability between 6.0 and 8.0.

2. An isolated 2-deoxy-scyllo-inosose synthase which is obtained by culturing
   a recombinant microorganism which comprises (a) an isolated nucleic acid of (i) or (ii), or (b) a recombinant vector which comprises the isolated nucleic acid of (i) or (ii):
   (i) an isolated nucleic acid encoding a 2-deoxy-scyllo-inosose synthase gene having a nucleotide sequence encoding any one of the following amino acid sequences:
      (a) amino acid sequences of SEQ ID NO: 2, 4, 6, and 8; and
      (b) an amino acid sequence having sequence identity of 95% or more with the amino acid sequence of SEQ ID NO: 2, and having temperature stability between 20° C. and 50° C. and/or pH stability between 6.0 to 8.0; or
   (ii) the isolated nucleic acid encoding a 2-deoxy-scyllo-inosose synthase gene having any of the following nucleotide sequences:
      (a) nucleotide sequences of SEQ ID NO: 1, 3, 5 and 7; and
      (b) an nucleotide sequence having sequence identity of 95% or more with the amino acid sequence of SEQ ID NO: 1, and having temperature stability between 20° C. and 50° C. and/or pH stability between 6.0 to 8.0.

3. A method for producing 2-deoxy-scyllo-inosose, comprising culturing the 2-deoxy-scyllo-inosose synthase according to claim 1 under conditions suitable to produce the 2-deoxy-scyllo-inosose.

4. The isolated 2-deoxy-scyllo-inosose synthase according to claim 1, having the amino acid sequences of SEQ ID NO: 2.

5. The isolated 2-deoxy-scyllo-inosose synthase according to claim 1, having the amino acid sequences of SEQ ID NO: 4.

6. The isolated 2-deoxy-scyllo-inosose synthase according to claim 1, having the amino acid sequences of SEQ ID NO: 6.

7. The isolated 2-deoxy-scyllo-inosose synthase according to claim 1, having the amino acid sequences of SEQ ID NO: 8.

8. The isolated 2-deoxy-scyllo-inosose synthase according to claim 2, which is obtained by culturing a recombinant microorganism which comprises (a) an isolated nucleic acid of (i) or (ii):
   (i) the isolated nucleic acid encoding a 2-deoxy-scyllo-inosose synthase gene having a nucleotide sequence encoding any one of the following amino acid sequences:
      (a) amino acid sequences of SEQ ID NO: 2, 4, 6, and 8; and
      (b) an amino acid sequence having sequence identity of 95% or more with the amino acid sequence of SEQ ID NO: 2, and having temperature stability between 20° C. and 50° C. and/or pH stability between 6.0 to 8.0; or
   (ii) the isolated nucleic acid encoding a 2-deoxy-scyllo-inosose synthase gene having any of the following nucleotide sequences:
      (a) nucleotide sequences of SEQ ID NO: 1, 3, 5 and 7; and
      (b) an nucleotide sequence having sequence identity of 95% or more with the amino acid sequence of SEQ ID NO: 1, and having temperature stability between 20° C. and 50° C. and/or pH stability between 6.0 to 8.0.

9. The isolated 2-deoxy-scyllo-inosose synthase according to claim 2, which is obtained by culturing a recombinant microorganism which comprises (a) an isolated nucleic acid of (i) or (ii):
   (i) the isolated nucleic acid encoding a 2-deoxy-scyllo-inosose synthase gene having a nucleotide sequence encoding any one of the following amino acid sequences:
      (a) amino acid sequences of SEQ ID NO: 2, 4, 6, and 8; or
   (ii) the isolated nucleic acid encoding a 2-deoxy-scyllo-inosose synthase gene having any of the following nucleotide sequences:
      (a) nucleotide sequences of SEQ ID NO: 1, 3, 5 and 7.

10. The isolated 2-deoxy-scyllo-inosose synthase according to claim 2, which is obtained by culturing a recombinant microorganism which comprises (a) an isolated nucleic acid of (i):
    (i) the isolated nucleic acid encoding a 2-deoxy-scyllo-inosose synthase gene having a nucleotide sequence encoding any one of the following amino acid sequences:
       (a) amino acid sequences of SEQ ID NO: 2, 4, 6, and 8.

11. The isolated 2-deoxy-scyllo-inosose synthase according to claim 2, which is obtained by culturing a recombinant microorganism which comprises (a) an isolated nucleic acid of (ii):

(ii) the isolated nucleic acid encoding a 2-deoxy-scyllo-inosose synthase gene having any of the following nucleotide sequences:
(a) nucleotide sequences of SEQ ID NO: 1, 3, 5 and 7.

12. The isolated 2-deoxy-scyllo-inosose synthase according to claim 2, which is obtained by culturing a recombinant microorganism which comprises (b) a recombinant vector which comprises the isolated nucleic acid of (i) or (ii):
(i) the isolated nucleic acid encoding a 2-deoxy-scyllo-inosose synthase gene having a nucleotide sequence encoding any one of the following amino acid sequences:
(a) amino acid sequences of SEQ ID NO: 2, 4, 6, and 8; and
(b) an amino acid sequence having sequence identity of 95% or more with the amino acid sequence of SEQ ID NO: 2, and having temperature stability between 20° C. and 50° C. and/or pH stability between 6.0 to 8.0; or
(ii) the isolated nucleic acid encoding a 2-deoxy-scyllo-inosose synthase gene having any of the following nucleotide sequences:
(a) nucleotide sequences of SEQ ID NO: 1, 3, 5 and 7; and
(b) an nucleotide sequence having sequence identity of 95% or more with the amino acid sequence of SEQ ID NO: 1, and having temperature stability between 20° C. and 50° C. and/or pH stability between 6.0 to 8.0.

13. The isolated 2-deoxy-scyllo-inosose synthase according to claim 2, which is obtained by culturing a recombinant microorganism which comprises (b) a recombinant vector which comprises the isolated nucleic acid of (i) or (ii):
(i) the isolated nucleic acid encoding a 2-deoxy-scyllo-inosose synthase gene having a nucleotide sequence encoding any one of the following amino acid sequences:
(a) amino acid sequences of SEQ ID NO: 2, 4, 6, and 8; or
(ii) the isolated nucleic acid encoding a 2-deoxy-scyllo-inosose synthase gene having any of the following nucleotide sequences:
(a) nucleotide sequences of SEQ ID NO: 1, 3, 5 and 7.

14. The isolated 2-deoxy-scyllo-inosose synthase according to claim 2, which is obtained by culturing a recombinant microorganism which comprises (b) a recombinant vector which comprises the isolated nucleic acid of (i):
(i) the isolated nucleic acid encoding a 2-deoxy-scyllo-inosose synthase gene having a nucleotide sequence encoding any one of the following amino acid sequences:
(a) amino acid sequences of SEQ ID NO: 2, 4, 6, and 8.

15. The isolated 2-deoxy-scyllo-inosose synthase according to claim 2, which is obtained by culturing a recombinant microorganism which comprises (b) a recombinant vector which comprises the isolated nucleic acid of (ii):
(ii) the isolated nucleic acid encoding a 2-deoxy-scyllo-inosose synthase gene having any of the following nucleotide sequences:
(a) nucleotide sequences of SEQ ID NO: 1, 3, 5 and 7.

* * * * *